United States Patent [19]

Nakagawa et al.

[11] Patent Number: 5,112,818

[45] Date of Patent: May 12, 1992

[54] 2-(2-CYCLOPROPYLPYRROLIDIN-4-YLTHIO)CARBAPENHEM DERIVATIVES

[75] Inventors: Susumu Nakagawa; Koji Yamada; Ryosuke Ushijima, all of Okazaki, Japan

[73] Assignee: Banyu Pharmaceutical Co., Ltd., Tokyo, Japan

[21] Appl. No.: 635,218

[22] Filed: Dec. 28, 1990

[30] Foreign Application Priority Data

Dec. 29, 1989 [JP] Japan .................... 1-342948

[51] Int. Cl.$^5$ .................... C07D 487/04; A61K 31/40
[52] U.S. Cl. .................... 514/210; 540/350
[58] Field of Search .................... 540/350; 514/210

[56] References Cited

U.S. PATENT DOCUMENTS

| | | | |
|---|---|---|---|
| 4.888.344 | 12/1989 | Suragawa et al. | 514/210 |
| 4,921,852 | 5/1990 | Murata et al. | 514/210 |
| 4,925,838 | 5/1990 | Murata et al. | 514/210 |
| 4,933,333 | 6/1990 | Sunagawa et al. | 514/210 |
| 4,962,103 | 10/1990 | Suragawa et al. | 540/350 |

FOREIGN PATENT DOCUMENTS

| | | |
|---|---|---|
| 10126587 | 11/1984 | European Pat. Off. . |
| 10182213 | 5/1986 | European Pat. Off. . |
| 243686 | 11/1987 | European Pat. Off. . |
| 10331175 | 9/1989 | European Pat. Off. . |

OTHER PUBLICATIONS

Journal of Medicinal Chemistry, Dec. 1979, pp. 1435-1436, vol. 22, No. 12; "N-Acetimidoyl-and-N-Formimidoylthienamycin Derivatives: Antipseudomonal . . .".

Journal of the American Chemical Society, Sep. 27, 1978, pp. 6491-6499; "Structure and Absolute Configuration of Thienamycin".

Antimicrobial Agents and Chemotherapy, Jul. 1982, pp. 62-70, vol. 22, No. 1; "Metabolism of Thienamycin and Related Carbapenem Antibiotics by the . . .".

Antimicrobial Agents and Chemotherapy, Feb. 1983, pp. 300-307, vol. 23, No. 2; "Urinary Recovery of N-Formimidoyl Thienamycin (MK0787) As Affected by . . .".

Journal of Antimicrobial Chemotherapy (1983), pp. 1-35; "Thienamycin: Development of Imipenem-Cilastatin".

Primary Examiner—Diana Rivers
Assistant Examiner—Jyothsna Venkat
Attorney, Agent, or Firm—Oblon, Spivak, McClelland, Maier & Neustadt

[57] ABSTRACT

A compound of the formula:

[Structure of formula (I) showing a carbapenem core with OH, $R^1$, CH$_3$, COOH, S-linked pyrrolidine with NH, cyclopropyl, $(CH_2)_n$—A—N($R^2$)($R^3$)]

wherein $R^1$ is a hydrogen atom or a methyl group, each of $R^2$ and $R^3$ which may be the same or different, is a hydrogen atom or a lower alkyl group, or $R^2$ and $R^3$ form together with the adjacent nitrogen atom a heterocyclic group selected from the group consisting of an aziridinyl group, an azetidinyl group, a pyrrolidinyl group, a piperidino group, a piperazinyl group and a morpholino group, A is a carbonyl group or a single bond, and n is an integer of from 0 to 3; or a pharmaceutically acceptable salt or ester thereof.

8 Claims, No Drawings

2-(2-CYCLOPROPYLPYRROLIDIN-4-YLTHIO)- CARBAPENHEM DERIVATIVES

The present invention relates to novel carbapenem (7-oxo-1-azabicyclo[3.2.0]hept-2-en-2-carboxylic acid) compounds, and antibacterial agents containing such compounds as active ingredients, and a process for producing such compounds.

In recent years, new β-lactam antibiotic substances have been found in nature which have the same β-lactam rings as penicillin derivatives and as cephalosporin derivatives, but which have different basic structures.

For example, naturally derived carbapenem compounds such as thienamycin isolated from the fermentation of Streptomyces cattleya (J. Am. Chem. Soc., vol. 100, p.6491 (1978)), are mentioned. Thienamycin has an excellent antibacterial spectrum and strong antibacterial activities over a wide range against gram positive bacteria and gram negative bacteria. Therefore, its development as a highly useful β-lactam agent has been expected. However, thienamycin itself is chemically unstable, and it has been reported that it is likely to be decomposed by a certain enzyme in vivo such as renal dehydropeptidase I (hereinafter referred to simply as DHP-I), whereby the antibacterial activities tend to decrease, and the recovery rate in the urine is low (Antimicrob. Agents Chemother., vol. 22, p.62 (1982); ditto, vol. 23, p.300 (1983)).

Merck & Co., Inc. have synthesized many thienamycin analogues with an aim to maintain the excellent antibacterial activities of thienamycin and to secure chemical stability. As a result, imipenem obtained by formimidation of the amino group of thienamycin, has been practically developed as a pharmaceutical product (J. Med. Chem., vol. 22, p. 1435 (1979)). Imipenem has antibacterial activities of an equal or higher level than thienamycin against various types of bacteria and has β-lactamase resistance. Especially against Pseudomonas aeruginosa, its antibacterial activities are superior to thienamycin by from 2 to 4 times. Further, the stability of imipenem in the solid form or in an aqueous solution is remarkably improved over thienamycin.

However, like thienamycin, imipenem is likely to be decomposed by DHP-I in the human kidney. Therefore, it can not be used for treatment of the urinary-tract infection. Further, it presents toxicity against the kidney due to the decomposition products. Therefore, imipenem can not be administered alone and is required to be used in combination with a DHP-I inhibitor like cilastatin (Antimicrob. Agents Chemother., vol. 12 (Suppl. D), p. 1 (1983)). In recent years, imipenem has been frequently used for the treatment and prevention of infectious diseases. Consequently, highly methicillin resistant Staphylococcus aureus which is resistant to imipenem and imipenem resistant Pseudomonas aeruginosa are increasing in the clinical field. Imipenem does not show adequate treating effects against these resistant bacteria.

As the prior art closest to the present invention, Japanese Examined Patent Publication No. 55514/1988 may be mentioned. This publication discloses carbapenem compounds having a 2-(aminocarbonyl or N-mono- or N,N-di-lower alkylaminocarbonyl)pyrrolidin-4-ylthio group at the 2-position of the carbapenem structure, represented by meropenem, SM-7338, as a typical compound.

β-Lactam antibiotics exhibit selective toxicity against bacteria and show no substantial effects against animal cells. Therefore, they are widely used for treatment of infectious diseases caused by bacteria, as rare antibiotics having little side effects, and thus are highly useful drugs.

However, in recent years, highly methicillin resistant Staphylococcus aureus and resistant Pseudomonas aeruginosa have been isolated frequently from patients with the immunity decreased, as bacteria causing hardly curable infectious diseases. This is regarded as a clinically serious problem. Accordingly, it is strongly desired to develop an antibacterial agent having improved antibacterial activities against such resistant bacteria. Especially with respect to carbapenem compounds, it is desired to improve the antibacterial activities, to improve the stability against DHP-I, to reduce the toxicity against the kidney and to reduce side effects against the central nervous system.

The compounds disclosed in Japanese Examined Patent Publication No. 55514/1988, particularly meropenem, have the stability against DHP-I substantially improved. However, the antibacterial activities against the abovementioned highly methicillin resistant Staphylococcus aureus are not adequate, and a carbapenem compound having superior antibacterial activities, is desired.

The carbapenem compounds having a 2-[(aminocarbonyl, aminocarbonyl lower alkyl, amino or amino lower alkyl)cyclopropyl]pyrrolidin-4-ylthio group at the 2-position of the carbapenem structure, as a feature of the present invention, are novel compounds, which have never been disclosed or suggested in any literatures or patent specifications.

The present inventors have made extensive researches with an aim to provide novel carbapenem compounds having excellent antibacterial activities particularly against highly methicillin resistant Staphylococcus aureus, which are resistant against DHP-I. As a result, they have found that novel carbapenem compounds having a 2-(aminocarbonyl, aminocarbonyl lower alkyl, amino or amino lower alkyl)cyclopropyl]-pyrrolidin-4-ylthio group at the 2-position of the carbapenem structure, have strong antibacterial activities against gram positive bacteria such as Staphylococcus aureus and against gram negative bacteria including Pseudomonas aeruginosa and further exhibit excellent stability against DHP-I. The present invention has been accomplished on the basis of this discovery.

The present invention provides a compound of the formula:

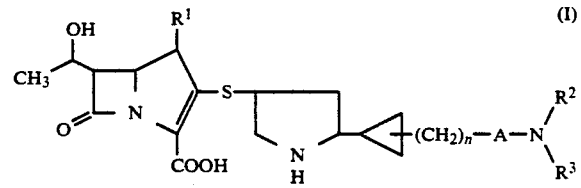

wherein $R^1$ is a hydrogen atom or a methyl group, each of $R^2$ and $R^3$ which may be the same or different, is a hydrogen atom or a lower alkyl group, or $R^2$ and $R^3$ form together with the adjacent nitrogen atom a heterocyclic group selected from the group consisting of an aziridinyl group, an azetidinyl group, a pyrrolidinyl group, a piperidino group, a piperazinyl group and a morpholino group, A is a carbonyl group or a single bond, and n is an integer of from 0 to 3; or a pharmaceutically acceptable salt or ester thereof.

The present invention also provides a process for producing the compound of the formula (I) or a pharmaceutically acceptable salt or ester thereof, which comprises reacting a compound of the formula:

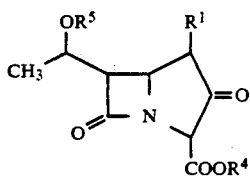
(II)

wherein R¹ is as defined above, R⁴ is a hydrogen atom or a carboxyl-protecting group, and R⁵ is a hydrogen atom or a hydroxyl-protecting group, or a reactive derivative thereof, with a compound of the formula:

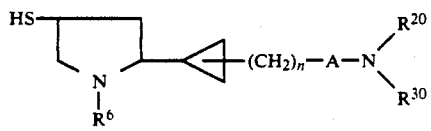

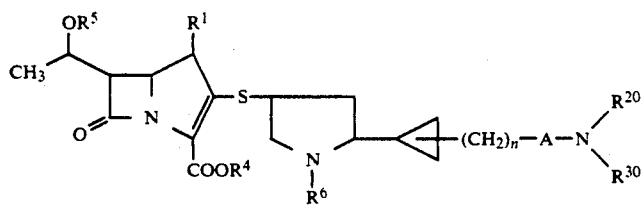
(IV)

wherein R¹, R⁴, R⁵, R⁶, R²⁰, R³⁰, A and n are as defined above, and if necessary, removing any protecting group of the compound of the formula (IV).

Further, the present invention provides an antibacterial agent comprising an antibacterially effective amount of the compound of the formula (I) or a pharmaceutically acceptable salt or ester thereof, and a pharmaceutically acceptable carrier or diluent.

Now, the present invention will be described in detail with reference to the preferred embodiments. Firstly, the symbols and terms used in this specification will be explained.

The compound of the present invention has a basic structure of the formula:

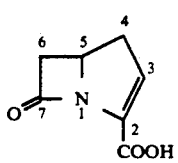

which is systematically referred to as a 7-oxo-1-azabicyclo[3.2.0]hept-2-en-2-carboxylic acid. For the convenience sake, in this specification, this basic structure will be referred to as a 1-carbapen-2-em-3-carboxylic acid by putting the numbers based on a commonly widely used carbapenem of the formula:

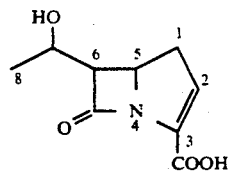

The present invention includes optical isomers based on the asymmetrical carbon atoms at the 1-position, 5-position, 6-position and 8-position of the carbapenem structure and stereoisomers. Among these isomers, preferred is a compound of a (5R,6S,8R) configuration i.e. a compound having a steric configuration of (5R,6S) (5,6-trans) like thienamycin and in which the carbon atom at the 8-position takes a R-configuration, or a compound of a (1R,5S,6S,8R) configuration in a case where a methyl group is present at the 1-position.

The 2'-[(aminocarbonyl, aminocarbonyl lower alkyl, amino or amino lower alkyl) cyclopropyl]pyrrolidin-4'-ylthio group at the 2-position of the carbapenem structure also includes isomers based on the asymmetrical carbon atoms at the 2- and 4-positions of the pyrrolidine structure. Among these isomers, preferred are compounds of a (2'S,4'S) configuration and a (2'R,4'R) configuration.

Accordingly, among compounds of the formula (I), a group of compounds having preferred steric configurations are represented by the formula (I-a):

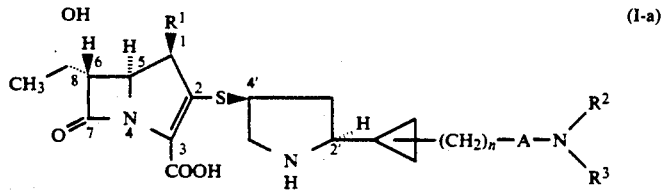
(I-a)

wherein R¹, R², R³, A and n are as defined above.

With respect to the steric configurations of a (aminocarbonyl, aminocarbonyl lower alkyl, amino or amino lower alkyl)cyclopropyl group on the cyclopropane ring, there exist cis and trans geometrical isomers. Such isomers are also included in the present invention.

The lower alkyl group means a linear or branched alkyl group having from 1 to 6 carbon atoms, preferably from 1 to 4 carbon atoms. Particularly preferred are a methyl group, an ethyl group and a tert-butyl group.

The carboxyl-protecting group may, for example, be a lower alkyl group such as a methyl group, an ethyl group, a propyl group, an isopropyl group or a tert-butyl group; a halogenated lower alkyl group such as a 2,2,2-trichloroethyl group or a 2,2,2-trifluoroethyl group; a lower alkanoyloxyalkyl group such as an acetoxymethyl group, a propionyloxymethyl group, a pivaloyloxymethyl group, a 1-acetoxyethyl group or a 1-propionyloxyethyl group; a lower alkoxycarbonyloxyalkyl group such as a 1-(methoxycarbonyloxy)ethyl group, a 1-(ethoxycarbonyloxy)ethyl group or a 1-(isopropoxycarbonyloxy)ethyl group; a lower alkenyl group such as a 2-propenyl group, a 2-chloro-2-propenyl group, a 3-methoxycarbonyl-2-propenyl group, a 2-methyl-2-propenyl group, a 2-butenyl group or a cinnamyl group; an aralkyl group such as a benzyl group, a p-methoxybenzyl group, a 3,4-dimethoxybenzyl group, an o-nitrobenzyl group, a p-nitrobenzyl group, a benzhydryl group or a bis(p-methoxyphenyl)methyl group; a (5-substituted 2-oxo-1,3-dioxol-4-yl)methyl group such as a (5-methyl-2-oxo-1,3-dioxol-4-yl)methyl group; a lower alkylsilyl group such as a trimethylsilyl group or a tertbutyldimethylsilyl group; an indanyl group, a phthalidyl group or a methoxymethyl group. Particularly preferred are a 2-propenyl group, a p-nitrobenzyl group, a p-methoxybenzyl group, a benzhydryl group and a tertbutyldimethylsilyl group.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a 2,4-dimethoxybenzyl group, an o-nitrobenzyl group, a p-nitrobenzyl group or a trityl group; an acyl group such as a formyl group or an acetyl group; a lower alkoxycarbonyl group such as a tert-butoxycarbonyl group, a 2-iodoethoxycarbonyl group or a 2,2,2-trichloroethoxycarbonyl group; an alkenyloxycarbonyl group such as a 2-propenyloxycarbonyl group, a 2-chloro2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; or an aralkyloxycarbonyl group such as a benzyloxycarbonyl group, a p-methoxybenzyloxycarbonyl group, an o-nitrobenzyloxycarbonyl group or a p-nitrobenzyloxycarbonyl group. Particularly preferred are a 2-propenyloxycarbonyl group, a p-nitrobenzyloxycarbonyl group and a tert-butyldimethylsilyl group.

The amino- or imino- protecting group may, for example, be an aralkylidene group such as a benzylidene group, a p-chlorobenzylidene group, a p-nitrobenzylidene group, a salicylidene group, an α-naphthylidene group or a β-naphthylidene group; an aralkyl group such as a benzyl group, a p-methoxybenzyl group, a 3,4-dimethoxybenzyl group, an o-nitrobenzyl group, a p-nitrobenzyl group, a benzhydryl group, a bis(p-methoxyphenyl)methyl group or a trityl group; a lower alkanoyl group such as a formyl group, an acetyl group, a propionyl group, butyryl group, an oxalyl group, a succinyl group, or a pivaloyl group; a halogenated lower alkanoyl group such as a chloroacetyl group, a dichloroacetyl group, a trichloroacetyl group or a trifluoroacetyl group; an arylalkanoyl group such as a phenylacetyl group or a phenoxyacetyl group; a lower alkoxycarbonyl group such as a methoxycarbonyl group, an ethoxycarbonyl group, a propoxycarbonyl group or a tertbutoxycarbonyl group; a halogenated lower alkoxycarbonyl group such as a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; an aralkyloxycarbonyl group such as a benzyloxycarbonyl group, an o-nitrobenzyloxycarbonyl group, a p-nitrobenzyloxycarbonyl group or a phenethyloxycarbonyl group; or a lower alkylsilyl group such as a trimethylsilyl group or a tert-butyldimethylsilyl group. Particularly preferred are a 2-propenyloxycarbonyl group, a tert-butoxycarbonyl group and a p-nitrobenzyloxycarbonyl group.

The meanings of abbreviations used in this specification are as follow:
Me: methyl group
Et: ethyl group
tBu: tert-butyl group
Pr: propyl group
iPr: isopropyl group Specific examples of the compound of the formula (I) will be given in the following Tables.

[I-b]

| No. | R¹ | R⁷ |
|---|---|---|
| 1 | H | NH₂ |
| 2 | H | NHMe |
| 3 | H | NHEt |
| 4 | H | NHPr |
| 5 | H | NH(iPr) |
| 6 | H | NH(tBu) |
| 7 | H | NMe₂ |
| 8 | H | NEt₂ |
| 9 | H | NPr₂ |
| 10 | H | N(iPr)₂ |
| 11 | H | N(tBu)₂ |
| 12 | H | N⟨triangle⟩ |
| 13 | H | N⟨square⟩ |
| 14 | H | N⟨pentagon⟩ |
| 15 | H | N⟨hexagon⟩ |

-continued

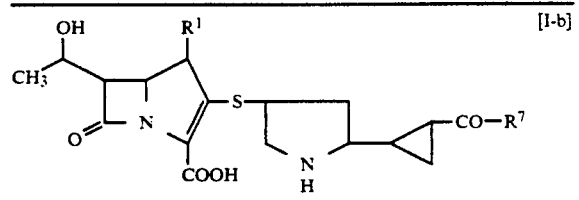
[I-b]

| No. | R¹ | R⁷ |
|---|---|---|
| 16 | H | (piperazine NH) |
| 17 | H | (piperazine NMe) |
| 18 | H | (morpholine) |
| 19 | Me | NH₂ |
| 20 | Me | NHMe |
| 21 | Me | NHEt |
| 22 | Me | NHPr |
| 23 | Me | NH(iPr) |
| 24 | Me | NH(tBu) |
| 25 | Me | NMe₂ |
| 26 | Me | NEt₂ |
| 27 | Me | ·NPr₂ |
| 28 | Me | N(iPr)₂ |
| 29 | Me | N(tBu)₂ |
| 30 | Me | (aziridine) |
| 31 | Me | (azetidine) |
| 32 | Me | (pyrrolidine) |
| 33 | Me | (piperidine) |
| 34 | Me | (piperazine NH) |
| 35 | Me | (piperazine NMe) |
| 36 | Me | (morpholine) |

Compounds of the formula:

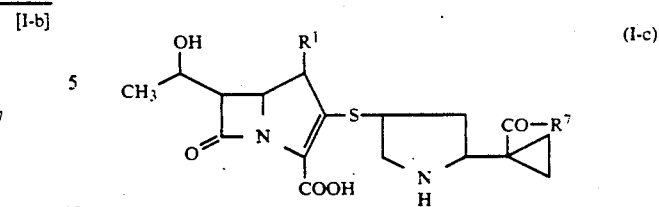
(I-c)

will be given in the following Table as specific examples of the compound of the formula (I) obtainable by the present invention.

| No. | R¹ | R⁷ |
|---|---|---|
| 37 | H | NH₂ |
| 38 | H | NHMe |
| 39 | H | NHEt |
| 40 | H | NHPr |
| 41 | H | NH(iPr) |
| 42 | H | NH(tBu) |
| 43 | H | NMe₂ |
| 44 | H | NEt₂ |
| 45 | H | NPr₂ |
| 46 | H | N(iPr)₂ |
| 47 | H | N(tBu)₂ |
| 48 | H | (aziridine) |
| 49 | H | (azetidine) |
| 50 | H | (pyrrolidine) |
| 51 | H | (piperidine) |
| 52 | H | (piperazine NH) |
| 53 | H | (piperazine NMe) |
| 54 | H | (morpholine) |
| 55 | Me | NH₂ |
| 56 | Me | NHMe |
| 57 | Me | NHEt |
| 58 | Me | NHPr |
| 59 | Me | NH(iPr) |
| 60 | Me | NH(tBu) |
| 61 | Me | NMe₂ |
| 62 | Me | NEt₂ |
| 63 | Me | NPr₂ |
| 64 | Me | N(iPr)₂ |
| 65 | Me | N(tBu)₂ |

-continued

| No. | R¹ | R⁷ |
|---|---|---|
| 66 | Me |  |
| 67 | Me | 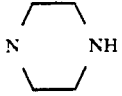 |
| 68 | Me |  |
| 69 | Me | 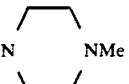 |
| 70 | Me |  |
| 71 | Me | 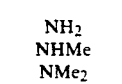 |
| 72 | Me |  |

Compounds of the formula:

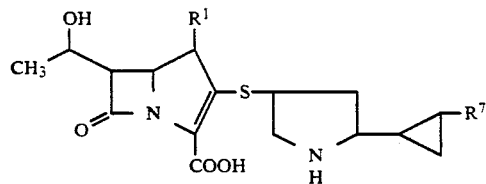

(I-d)

will be given in the following Table as specific examples of the compound of the formula (I) obtainable by the present invention.

| No. | R¹ | R⁷ |
|---|---|---|
| 73 | H | NH₂ |
| 74 | H | NHMe |
| 75 | H | NHEt |
| 76 | H | NMe₂ |
| 77 | H | 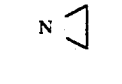 |
| 78 | H | 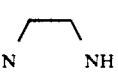 |

-continued

| No. | R¹ | R⁷ |
|---|---|---|
| 79 | H | 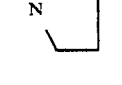 |
| 80 | H | 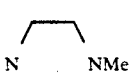 |
| 81 | Me | NH₂ |
| 82 | Me | NHMe |
| 83 | Me | NMe₂ |
| 84 | Me | 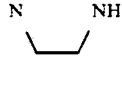 |
| 85 | Me | 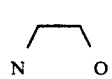 |
| 86 | Me | 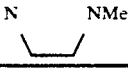 |
| 87 | Me |  |

Compounds of the formula:

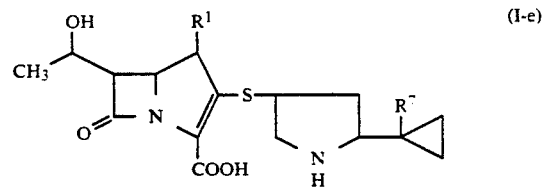

(I-e)

will be given in the following Table as specific examples of the compound of the formula (I) obtainable by the present invention.

| No. | R¹ | R⁷ |
|---|---|---|
| 88 | H | NH₂ |
| 89 | H | NHMe |
| 90 | H | NMe₂ |
| 91 | H |  |
| 92 | H |  |
| 93 | H |  |

-continued

| No. | $R^1$ | $R^7$ |
|---|---|---|
| 94 | H | 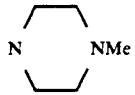 |
| 95 | Me | $NH_2$ |
| 96 | Me | NHMe |
| 97 | Me | $NMe_2$ |
| 98 | Me | 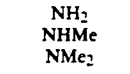 |
| 99 | Me |  |
| 100 | Me | 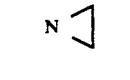 |
| 101 | Me | 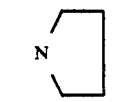 |

Compounds of the formula:

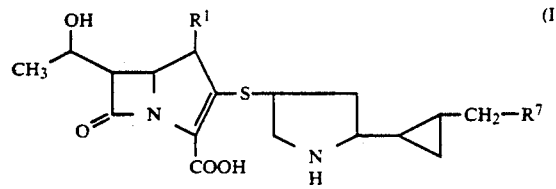

(I-f)

will be given in the following Table as specific examples of the compound of the formula (I) obtainable by the present invention.

| No. | $R^1$ | $R^7$ |
|---|---|---|
| 102 | H | $NH_2$ |
| 103 | H | NHMe |
| 104 | H | $NMe_2$ |
| 105 | H | 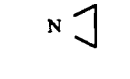 |
| 106 | H | 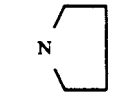 |
| 107 | H | 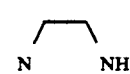 |
| 108 | H | 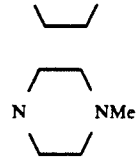 |
| 109 | Me | $NH_2$ |

-continued

| No. | $R^1$ | $R^7$ |
|---|---|---|
| 110 | Me | NHMe |
| 111 | Me | $NMe_2$ |
| 112 | Me |  |
| 113 | Me |  |
| 114 | Me |  |
| 115 | Me |  |

Compounds of the formula:

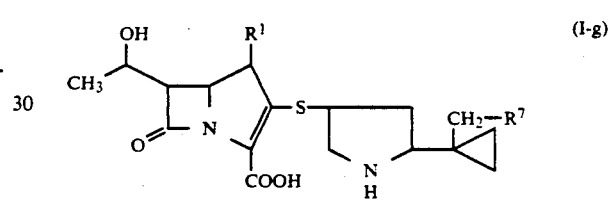

(I-g)

will be given in the following Table as specific examples of the compound of the formula (I) obtainable by the present invention.

| No. | $R^1$ | $R^7$ |
|---|---|---|
| 116 | H | $NH_2$ |
| 117 | H | NHMe |
| 118 | H | $NMe_2$ |
| 119 | H |  |
| 120 | H |  |
| 121 | H |  |
| 122 | H |  |
| 123 | Me | $NH_2$ |
| 124 | Me | NHMe |
| 125 | Me | $NMe_2$ |
| 126 | Me |  |

-continued

| No. | R¹ | R⁷ |
|---|---|---|
| 127 | Me |  (azetidine) |
| 128 | Me | 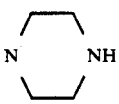 (N─NH piperazine) |
| 129 | Me | 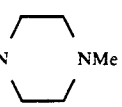 (N─NMe piperazine) |

Compounds of the formula:

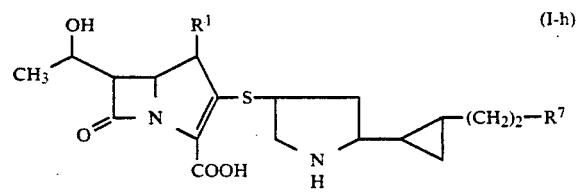

(I-h)

will be given in the following Table as specific examples of the compound of the formula (I) obtainable by the present invention.

| No. | R¹ | R⁷ |
|---|---|---|
| 130 | H | NH₂ |
| 131 | H | NHMe |
| 132 | H | NMe₂ |
| 133 | H |  (aziridine) |
| 134 | H | 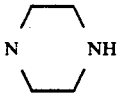 (azetidine) |
| 135 | H | 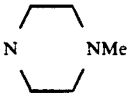 (N─NH piperazine) |
| 136 | H |  (N─NMe piperazine) |
| 137 | Me | NH₂ |
| 138 | Me | NHMe |
| 139 | Me | NMe₂ |
| 140 | Me |  (aziridine) |
| 141 | Me |  (azetidine) |
| 142 | Me | 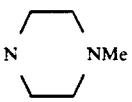 (N─NH piperazine) |
| 143 | Me |  (N─NMe piperazine) |

Compounds of the formula:

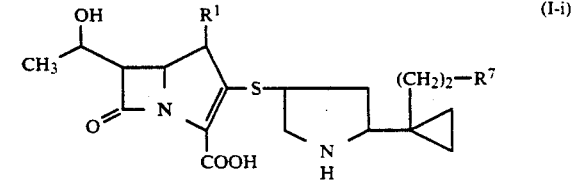

(I-i)

will be given in the following Table as specific examples of the compound of the formula (I) obtainable by the present invention.

| No. | R¹ | R⁷ |
|---|---|---|
| 144 | H | NH₂ |
| 145 | H | NHMe |
| 146 | H | NMe₂ |
| 147 | H |  (aziridine) |
| 148 | H |  (azetidine) |
| 149 | H |  (N─NH piperazine) |
| 150 | H |  (N─NMe piperazine) |
| 151 | Me | NH₂ |
| 152 | Me | NHMe |
| 153 | Me | NMe₂ |
| 154 | Me |  (aziridine) |
| 155 | Me |  (azetidine) |
| 156 | Me |  (N─NH piperazine) |

| No. | R¹ | R⁷ |
|---|---|---|
| 157 | Me | N⌢NMe (piperazinyl) |

Compounds of the formula:

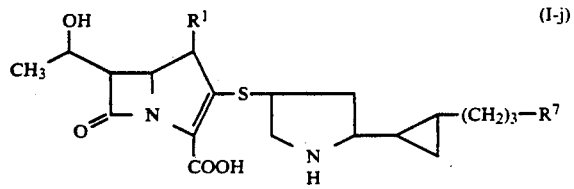

(I-j)

will be given in the following Table as specific examples of the compound of the formula (I) obtainable by the present invention.

| No. | R¹ | R⁷ |
|---|---|---|
| 158 | H | NH₂ |
| 159 | H | NHMe |
| 160 | H | NMe₂ |
| 161 | H | N▷ (aziridinyl) |
| 162 | H | azetidinyl |
| 163 | H | piperazinyl-NH |
| 164 | H | piperazinyl-NMe |
| 165 | Me | NH₂ |
| 166 | Me | NHMe |
| 167 | Me | NMe₂ |
| 168 | Me | N▷ |
| 169 | Me | azetidinyl |
| 170 | Me | piperazinyl-NH |
| 171 | Me | piperazinyl-NMe |

Compounds of the formula:

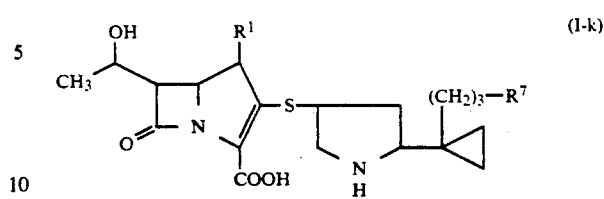

(I-k)

will be given in the following Table as specific examples of the compound of the formula (I) obtainable by the present invention.

| No. | R¹ | R⁷ |
|---|---|---|
| 172 | H | NH₂ |
| 173 | H | NHMe |
| 174 | H | NMe₂ |
| 175 | H | N▷ |
| 176 | H | azetidinyl |
| 177 | H | piperazinyl-NH |
| 178 | H | piperazinyl-NMe |
| 179 | Me | NH₂ |
| 180 | Me | NHMe |
| 181 | Me | NMe₂ |
| 182 | Me | N▷ |
| 183 | Me | azetidinyl |
| 184 | Me | piperazinyl-NH |
| 185 | Me | piperazinyl-NMe |

Compounds of the formula:

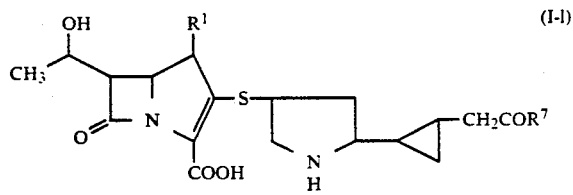  (I-l)

will be given in the following Table as specific examples of the compound of the formula (I) obtainable by the present invention.

| No. | $R^1$ | $R^7$ |
|---|---|---|
| 186 | H | $NH_2$ |
| 187 | H | NHMe |
| 188 | H | $NMe_2$ |
| 189 | H | N-aziridinyl |
| 190 | H | N-pyrrolidinyl |
| 191 | H | N-piperazinyl (NH) |
| 192 | H | N-piperazinyl (NMe) |
| 193 | Me | $NH_2$ |
| 194 | Me | NHMe |
| 195 | Me | $NMe_2$ |
| 196 | Me | N-aziridinyl |
| 197 | Me | N-pyrrolidinyl |
| 198 | Me | N-piperazinyl (NH) |
| 199 | Me | N-piperazinyl (NMe) |

Compounds of the formula:

(I-m)

will be given in the following Table as specific examples of the compound of the formula (I) obtainable by the present invention.

| No. | $R^1$ | $R^7$ |
|---|---|---|
| 200 | H | $NH_2$ |
| 201 | H | NHMe |
| 202 | H | $NMe_2$ |
| 203 | H | N-aziridinyl |
| 204 | H | N-pyrrolidinyl |
| 205 | H | N-piperazinyl (NH) |
| 206 | H | N-piperazinyl (NMe) |
| 207 | Me | $NH_2$ |
| 208 | Me | NHMe |
| 209 | Me | $NMe_2$ |
| 210 | Me | N-aziridinyl |
| 211 | Me | N-pyrrolidinyl |
| 212 | Me | N-piperazinyl (NH) |
| 213 | Me | N-piperazinyl (NMe) |

Compounds of the formula:

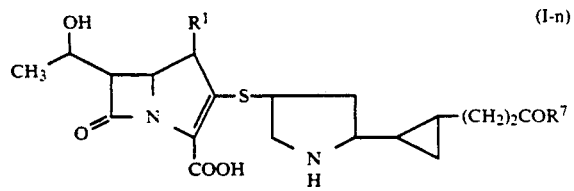

(I-n)

will be given in the following Table as specific examples of the compound of the formula (I) obtainable by the present invention.

| No. | R¹ | R⁷ |
|---|---|---|
| 214 | H | $NH_2$ |
| 215 | H | NHMe |
| 216 | H | $NMe_2$ |
| 217 | H | N⊲ (aziridinyl) |
| 218 | H | azetidinyl |
| 219 | H | piperazinyl (NH) |
| 220 | H | N-methylpiperazinyl (NMe) |
| 221 | Me | $NH_2$ |
| 222 | Me | NHMe |
| 223 | Me | $NMe_2$ |
| 224 | Me | N⊲ (aziridinyl) |
| 225 | Me | azetidinyl |
| 226 | Me | piperazinyl (NH) |
| 227 | Me | N-methylpiperazinyl (NMe) |

Compounds of the formula:

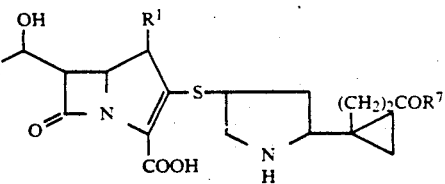

(I-o)

will be given in the following Table as specific examples of the compound of the formula (I) obtainable by the present invention.

| No. | R¹ | R⁷ |
|---|---|---|
| 228 | H | $NH_2$ |
| 229 | H | NHMe |
| 230 | H | $NMe_2$ |
| 231 | H | $NEt_2$ |
| 232 | H | N⊲ (aziridinyl) |
| 233 | H | azetidinyl |
| 234 | H | piperazinyl (NH) |
| 235 | H | N-methylpiperazinyl (NMe) |
| 236 | Me | $NH_2$ |
| 237 | Me | NHMe |
| 238 | Me | $NMe_2$ |
| 239 | Me | N⊲ (aziridinyl) |
| 240 | Me | azetidinyl |
| 241 | Me | piperazinyl (NH) |
| 242 | Me | N-methylpiperazinyl (NMe) |

Compounds of the formula:

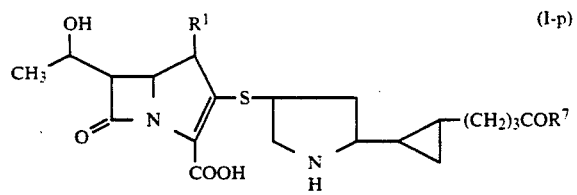

(I-p)

will be given in the following Table as specific examples of the compound of the formula (I) obtainable by the present invention.

| No. | $R^1$ | $R^7$ |
|---|---|---|
| 243 | H | $NH_2$ |
| 244 | H | NHMe |
| 245 | H | $NMe_2$ |
| 246 | H | N-aziridinyl |
| 247 | H | N-azetidinyl |
| 248 | H | piperazinyl (NH) |
| 249 | H | piperazinyl (NMe) |
| 250 | Me | $NH_2$ |
| 251 | Me | NHMe |
| 252 | Me | $NMe_2$ |
| 253 | Me | N-aziridinyl |
| 254 | Me | N-azetidinyl |
| 255 | Me | piperazinyl (NH) |
| 256 | Me | piperazinyl (NMe) |

Compounds of the formula:

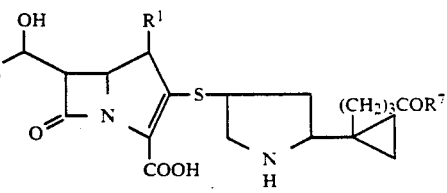

(I-q)

will be given in the following Table as specific examples of the compound of the formula (I) obtainable by the present invention.

| No. | $R^1$ | $R^7$ |
|---|---|---|
| 257 | H | $NH_2$ |
| 258 | H | NHMe |
| 259 | H | $NMe_2$ |
| 260 | H | N-aziridinyl |
| 261 | H | N-azetidinyl |
| 262 | H | piperazinyl (NH) |
| 263 | H | piperazinyl (NMe) |
| 264 | Me | $NH_2$ |
| 265 | Me | NHMe |
| 266 | Me | $NMe_2$ |
| 267 | Me | N-aziridinyl |
| 268 | Me | N-azetidinyl |
| 269 | Me | piperazinyl (NH) |
| 270 | Me | piperazinyl (NMe) |

Among the above specific compounds, particularly preferred are the following compounds: (5S,6S)-2-[(2S,4S)-2-[2-(aminocarbonyl)cyclopropyl]pyrrolidin-4-ylthio]-6-[(R)-1-hydroxyethyl]-1-carbapen2-em-3-carboxylic acid(compound 1), (5S,6S)-6-[(R)-1-hydroxyethyl]-2-[(2S,4S)-2-[2-(N-methylaminocarbonyl) cyclopropyl]pyrrolidin-4-ylthio]-1-carbapen-2-em-3-carboxylic acid(compound 2), (5S,6S)-6-[(R)-1-hydroxyethyl]-2-[(2S,4S)-2-[2-(N,N-dimethylaminocarbonyl) cyclopropyl]pyrrolidin-4-ylthio]1-carbapen-2-em-3-carboxylic acid(compound 7), (5S,6S)-2-[(2S,4S)-2-[2-(1-azetidinylcarbonyl)cyclopropyl]pyrrolidin-4-ylthio]-6-[(R)-1-hydroxyethyl]-1-carbapen-2-em-3-carboxylic acid(compound 13), (5S,6S)-6-[(R)-1-hydroxyethyl]-2-[(2S,4S)-2-[2-(1-pyrrolidinylcarbonyl) cyclopropyl]pyrrolidin-4-ylthio]-1-carbapen-2-em-3-carboxylic acid(compound 14), (5S,6S)-6-[(R)-1-hydroxyethyl]-2-[(2S,4S)-2-[2-(1-piperazinylcarbonyl) cyclopropyl]pyrrolidin-4-ylthio]-1-carbapen-2-em-3-carboxylic acid(compound 16), (1R,5S,6S)-2-[(2S,4S)-2-[2-(aminocarbonyl)cyclopropyl]-pyrrolidin-4-ylthio]-6-[(R)-1-hydroxyethyl]-1-methyl-1-carbapen-2-em-3-carboxylic acid(compound 19), (1R,5S,6S)-6-[(R)-1-hydroxyethyl]-1-methyl-2-[(2S,4S)-2-[2-(N-methylaminocarbonyl)cyclopropyl]pyrrolidin-4-yl-thio]-1-carbapen-2-em-3-carboxylic acid(compound 20), (1R,5S,6S)-2-[(2S,4S)-2-[2-(N,N-dimethylaminocarbonyl)-cyclopropyl]pyrrolidin-4-ylthio]-6-[(R)-1-hydroxyethyl]-1-methyl-1-carbapen-2-em-3-carboxylic acid(compound 25), (1R,5S,6S)-2-[(2S,4S)-2-[2-(1-aziridinylcarbonyl)cyclo-propyl]pyrrolidin-4-ylthio]-6-[(R)-1-hydroxyethyl]-1-methyl-1-carbapen-2-em-3-carboxylic acid(compound 30), (1R,5S,6S)-2-[(2S,4S)-2-[2-(1-azetidinylcarbonyl)cyclopropyl]pyrrolidin-4-ylthio]-6-[(R)-1-hydroxyethyl]-1-methyl-1-carbapen-2-em-3-carboxylic acid(compound 31), (1R,5S,6S)-6-[(R)-1-hydroxyethyl]-1-methyl-2-[(2S,4S)-2-[2-(1-pryyolidinylcarbonyl) cyclopropyl]-pyrrolidin-4-yl-thio]-1-carbapen-2-em-3-carboxylic acid(compound 32), (1R,5S,6S)-6-[(R)-1-hydroxyethyl]-1-methyl-2-[(2S,4S)-2-[2-(1-piperazinylcarbonyl)cyclopropyl]pyrrolidin-4-yl-thio]-1-carbapen-2-em-3-carboxylic acid(compound 34), (5S,6S)-2-[(2S,4S)-2-[1-(aminocarbonyl)cyclopropyl]pyrrolidin-4-ylthio]-6-[(R)-1-hydroxyethyl]-1-carbapen2-em-3-carboxylic acid(compound 37), (5S,6S)-6-[(R)-1-hydroxyethyl]-2-[(2S,4S)-2-[1-(N-methylaminocarbonyl)cyclopropyl]pyrrolidin-4-ylthio]-1-carbapen-2-em-3-carboxylic acid(compound 38), (5S,6S)-2-[(2S,4S)-2-[1-(N,N-dimethylaminocarbonyl)-cyclopropyl]pyrrolidin-4-ylthio]-6-[(R)-1-hydroxyethyl]1-carbapen-2-em-3-carboxylic acid(compound 43), (5S,6S)-2-[(2S,4S)-2-[1-(1-azetidinylcarbonyl)cyclopropyl]pyrrolidin-4-ylthio]-6-[(R)-1-hydroxyethyl]-1-carbapen-2-em-3-carboxylic acid(compound 49), (5S,6S)-6-[(R)-1-hydroxyethyl]-2-[(2S,4S)-2-[1-(1-pyrrolidinylcarbonyl) cyclopropyl]pyrrolidin-4-ylthio]-1-carbapen-2-em-3-carboxylic acid(compound 50), (5S,6S)-6-[(R)-1-hydroxyethyl]-2-[(2S,4S)-2-[1-(1-piperazinylcarbonyl) cyclopropyl]pyrrolidin-4-ylthio]-1-carbapen-2-em-3-carboxylic acid(compound 52), (1R,5S,6S)-2-[(2S,4S)-2-[1-(aminocarbonyl)cyclopropyl]-pyrrolidin-4-ylthio]-6-[(R)-1-hydroxyethyl]-1-methyl-1-carbapen-2-em-3-carboxylic acid(compound 55), (1R,5S,6S)-6-[(R)-1-hydroxyethyl]-1-methyl-2-[(2S,4S)-2-[1-(N-methylaminocarbonyl)cyclopropyl]pyrrolidin-4-yl-thio]-1-carbapen-2-em-3-carboxylic acid(compound 56), (1R,5S,6S)-2-[(2S,4S)-2-[1-(N,N-dimethylaminocarbonyl)cyclopropyl]pyrrolidin-4-ylthio]-6-[(R)-1-hydroxyethyl]-1-methyl-1-carbapen-2-em-3-carboxylic acid(compound 61), (1R,5S,6S)-2-[(2S,4S)-2-[1-(1-azetidinylcarbonyl)c yclopropyl]pyrrolidin-4-ylthio]-6-[(R)-1-hydroxyethyl]-1-methyl-1-carbapen-2-em-3-carboxylic acid(compound 67), (1R,5S,6S)-6-[(R)-1-hydroxyethyl]-1-methyl-2-[(2S,4S)-2-[1-(1-pyrrolidinylcarbonyl)cyclopropyl]pyrrolidin-4-yl-thio]-1-carbapen-2-em-3-carboxylic acid(compound 68), (1R,5S,6S)-6-[(R)-1-hydroxyethyl]-1-methyl-2-[(2S,4S)-2-[1-(1-piperazinylcarbonyl)cyclopropyl]-pyrrolidin-4-yl-thio]-1-carbapen-2-em-3-carboxylic acid(compound 70), (5S,6S)-2-[(2S,4S)-2-(2-aminocyclopropyl)pyrrolidin-4-ylthio]-6-[(R)-1-hydroxyethyl]-1-carbapen-2-em-3-carboxylic acid(compound 73), (5S,6S)-6-[(R)-1-hydroxyethyl]-2-[(2S,4S)-2-[2-(N-methylamino) cyclopropyl]pyrrolidin-4-ylthio]-1-carbapen2-em-3-carboxylic acid(compound 74), (5S,6S)-2-[(2S,4S)-2-[2-(N,N-dimethylamino)cyclopropyl]pyrrolidin-4-ylthio]-6-[(R)-1-hydroxyethyl]-1-carbapen2-em-3-carboxylic acid(compound 76), (5S,6S)-6-[(R)-1-hydroxyethyl]-2-[(2S,4S)-2-[2-(1-piperazinyl) cyclopropyl]pyrrolidin-4-ylthio]-1-carbapen2-em-3-carboxylic acid(compound 79), (1R,5S,6S)-2-[(2S,4S)-2-(2-aminocyclopropyl)pyrrolidin-4-ylthio]-6-[(R)-1-hydroxyethyl]-1-methyl-1-carbapen-2-em-3-carboxylic acid(compound 81), (1R,5S,6S)-6-[(R)-1-hydroxyethyl]-1-methyl-2-[(2S,4S)-2-[2-(N-methylamino)cyclopropyl]pyrrolidin-4-ylthio]-1-carbapen-2-em-3-carboxylic acid(compound 82), (1R,5S,6S)-2-[(2S,4S)-2-[2-(N,N-dimethylamino)cyclopropyl]pyrrolidin-4-ylthio]-6-[(R)-1-hydroxyethyl]-1-methyl-1-carbapen-2-em-3-carboxylic acid(compound 83), (1R,5S,6S)-6-[(R)-1-hydroxyethyl]-1-methyl-2-[(2S,4S)-2-[2-(1-piperazinyl)-cyclopropyl]pyrrolidin-4-ylthio]-1-carbapen-2-em-3-carboxylic acid(compound 86), (5S,6S)-2-[(2S,4S)-2-(1-aminocyclopropyl)pyrrolidin-4-ylthio]-6-[(R)-1-hydroxyethyl]-1-carbapen-2-em-3-carboxylic acid(compound 88), (5S,6S)-6-[(R)-1-hydroxyethyl]-2-[(2S,4S)-2-[1-(N-methylamino) cyclopropyl]pyrrolidin-4-ylthio]-1-carbapen-2-em-3-carboxylic acid(compound 89), (5S,6S)-2-[(2S,4S)-2-[1-(N,N-dimethylamino)cyclopropyl]-pyrrolidin-4-ylthio]-6-[(R)-1-hydroxyethyl]-1-carbapen-2-em-3-carboxylic acid(compound 90), (1R,5S,6S)-6-[(R)-1-hydroxyethyl]-1-methyl-2-[(2S,4S)-2-[1-(1-piperazinyl)cyclopropyl]pyrrolidin-4-ylthio]-1-carbapen-2-em-3-carboxylic acid(compound 93), (1R,5S,6S)-2-[(2S,4S)-2-(1-aminocyclopropyl)pyrrolidin-4-ylthio]-6-[(R)-1-hydroxyethyl]-1-methyl-1-carbapen-2-em-3-carboxylic acid(compound 95), (1R,5S,6S)-6-[(R)-1-hydroxyethyl]-1-methyl-2-[(2S,4S)-2-[1-(N-methylamino)cyclopropyl]pyrrolidin-4-ylthio]-1-carbapen 2-em-3-carboxylic acid(compound 96), (1R,5S,6S)-2-[(2S,4S)-2-[1-(N,N-dimethylamino)cyclopropyl]pyrrolidin-4-ylthio]-6-[(R)-1-hydroxyethyl]-1-methyl-1-carbapen-2-em-3-carboxylic acid(compound 97), (1R,5S,6S)-6-[(R)-1-hydroxyethyl]-1-methyl-2-[(2S,4S)-2-[1-(1-piperazinyl)cyclopropyl]pyrrolidin-4-ylthio]-1-carbapen-2-em-3-carboxylic acid(compound 100), (5S,6S)-2-[(2S,4S)-2-[2-(aminomethyl)cyclopropyl]pyrrolidin-4-ylthio]-6-[(R)-1-hydroxyethyl]-1-carbapen-2-em-3-carboxylic acid(compound 102), (5S,6S)-6-[(R)-1-hydroxyethyl]-2-[(2S,4S)-2-[2-(N-methylaminomethyl) cyclopropyl]pyrrolidin-4-ylthio]-1-carbapen-2-em-3 carboxylic acid(compound 103), (5S,6S)-2-[(2S,4S)-2-[2-(N,N-dimethylaminomethyl)cyclopropyl]pyrrolidin-4-ylthio]-6-[(R)-1-hydroxyethyl]-1-carbapen-2-em-3-carboxylic acid(compound 104), (5S,6S)-6-[(R)-1-hydroxyethyl]-2-[(2S,4S)-2-[2-(1-piperazinylmethyl) cyclopropyl]pyrrolidin-4-ylthio]-1-carbapen-2-em-3-carboxylic acid(compound 107), (1R,5S,6S)-2-[(2S,4S)-2-[2-(aminomethyl)cyclopropyl]-pyrrolidin-4-ylthio]-6-[(R)-1-hydroxyethyl]-1-methyl-1-carbapen-2-em-3-carboxylic acid(compound 109), (1R,5S,6S)-6-[(R)-1-hydroxyethyl]-1-methyl-2-[(2S,4S)-2-[2-(N-methylaminomethyl)cyclopropyl]pyrrolidin-4-yl-thio]-1-carbapen-2-em-3-carboxylic acid(compound 110), (1R,5S,6S)-2-[(2S,4S)-2-[2-(N,N-dimethylaminomethyl)cyclopropyl]pyrrolidin-4-ylthio]-6-[(R)-1-hydroxyethyl]-1-methyl-1-carbapen-2-em-3-carboxylic acid(compound 111), (1R,5S,6S)-6-[(R)-1-hydroxyethyl]-1-methyl-2-[(2S,4S)-2-[2-(1-piperazinylmethyl)cyclopropyl]pyrrolidin-4-ylthio]-1-carbapen-2-em-3-carboxylic acid(compound 114), (5S,6S)-2-[(2S,4S)-2-[1-(aminomethyl)cyclopropyl]pyrrolidin-4-ylthio]-6-[(R)-1-hydroxyethyl]-1-carbapen2-em-3-carboxylic acid(compound 116), (5S,6S)-6-[(R)-1-hydroxyethyl]-2-[(2S,4S)-2-[1-(N-methylaminomethyl) cyclopropyl]pyrrolidin-4-ylthio]-1-carbapen-2-em-3-carboxylic acid(compound 117), (5S,6S)-2-[(2S,4S)-2-[1-(N,N-dimethylaminomethyl)cyclopropyl]pyrrolidin-4-ylthio]-6-[(R)-1-hydroxyethyl]-1-carbapen-2-em-3-carboxylic acid(compound 118), (1R,5S,6S)-6-[(R)-1-hydroxyethyl]-1-methyl-2-[(2S,4S)-2-[1-(1-piperazinylmethyl)cyclopropyl]pyrrolidin-4-yl-thio] -1-carbapen-2-em-3-carboxylic acid(compound 121), (1R,5S,6S)-2-[(2S,4S)-2-[1-(aminomethyl)cyclopropyl]pyrrolidin-4-ylthio]-6-[(R)-1-hydroxyethyl]-1-methyl-1-carbapen-2-em-3-carboxylic acid(compound 123), (1R,5S,6S)-6-[(R)-1-hydroxyethyl]-1-methyl-2-[(2S,4S)-2-[1-(N-methylaminomethyl)cyclopropyl]pyrrolidin-4-yl-thio]-1-carbapen-2-em-3-carboxylic acid(compound 124), (1R,5S,6S)-2-[(2S,4S)-2-[1-(N,N-dimethylaminomethyl)cyclopropyl]pyrrolidin-4-ylthio]-6-[(R)-1-hydroxyethyl]-1-methyl-1-carbapen-2-em-3-carboxylic acid(compound 125), (1R,5S,6S)-6-[(R)-1-hydroxyethyl]-1-methyl-2-[(2S,4S)-2-[1-(1-piperazinylmethyl)cyclopropyl]pyrrolidin-4-yl-thio]-1-carbapen-2-em-3-carboxylic acid(compound 128), (5S,6S)-2-[(2S,4S)-2-[2-(2-aminoethyl)cyclopropyl]pyrrolidin-4-ylthio]-6-[(R)-1-hydroxyethyl]-1-carbapen-2-em-3-carboxylic acid(compound 130), (1R,5S,6S)-2-[(2S,4S)-2-[2-(2-aminoethyl)cyclopropyl]pyrrolidin-4-ylthio]-6-[(R)-1-hydroxyethyl]-1-methyl-1-carbapen-2-em-3-carboxylic acid(compound 137), (5S,6S)-2-[(2S,4S)-2-[1-(2-aminoethyl)cyclopropyl]pyrrolidin-4-ylthio]-6-[(R)-1-hydroxyethyl]-1-carbapen-2-em-3-carboxylic acid(compound 144), (1R,5S,6S)-2-[(2S,4S)-2-[1-(2-aminoethyl)cyclopropyl]pyrrolidin-4-ylthio]-6-[(R)-1-hydroxyethyl]-1-methyl-1-carbapen-2-em-3-carboxylic acid(compound 151), (5S,6S)-2-[(2S,4S)-2-[2-(3-aminopropyl)cyclopropyl]pyrrolidin-4-ylthio] -6-[(R)-1-hydroxyethyl]-1-carbapen2-em-3-carboxylic acid(compound 158), (1R,5S,6S)-2-[(2S,4S)-2-[2-(3-aminopropyl)cyclopropyl]pyrrolidin-4-ylthio]-6-[(R)-1-hydroxyethyl]-1-methyl-1-carbapen-2-em-3-carboxylic acid(compound 165), (5S,6S)-2-[(2S,4S)-2-[1-(3-aminopropyl)cyclopropyl]pyrrolidin-4-ylthio]-6-[(R)-1-hydroxyethyl]-1-carbapen2-em-3-carboxylic acid(compound 172), (1R,5S,6S)-2-[(2S,4S)-2-[1-(3-aminopropyl)cyclopropyl]pyrrolidin-4-ylthio]-6-[(R)-1-hydroxyethyl]-1-methyl-1-carbapen-2-em-3-carboxylic acid(compound 179), (1R,5S,6S)-6-[(R)-1-hydroxyethyl]-1-methyl-2-[(2S,4S)-2-[1-(3-N-methylaminopropyl)cyclopropyl]-pyrrolidin-4-yl-thio]-1-carbapen-2-em-3-carboxylic acid(compound 180), (1R,5S,6S)-2-[(2S,4S)-2-[1-(3-N,N-dimethylaminopropyl)cyclopropyl]pyrrolidin-4-ylthio]-6-[(R)-1-hydroxyethyl]-1-methyl-1-carbapen-2-em-3-carboxylic acid(compound 181), (1R,5S,6S)-6-[(R)-1-hydroxyethyl]-1-methyl-2-[(2S,4S)-2-[1-[3-(1-pyrrolidinyl)propyl]cyclopropyl]pyrrolidin-4-ylthio]-1-carbapen-2-em-3-carboxylic acid(compound 183), (5R,6S)-2-[(2S,4S)-2-[2-(aminocarbonylmethyl)cyclo propyl]pyrrolidin-4-ylthio]-6-[(R)-1-hydroxyethyl]-1-carbapen-2-em-3-carboxylic acid(compound 186), (5R,6S)-6-[(R)-1-hydroxyethyl]-2-[(2S,4S)-2-[2-(N-methylaminocarbonylmethyl) cyclopropyl]pyrrolidin-4-yl-thio] -1-carbapen-2-em-3-carboxylic acid(compound 187), (5R,6S)-2-[(2S,4S)-2-[2-(N,N-dimethylaminocarbonyl methyl)cyclopropyl]pyrrolidin-4-ylthio]-6-[(R)-1-hydroxyethyl]-1-carbapen-2-em-3-carboxylic acid (compound 188), (5R,6S)-6-[(R)-1-hydroxyethyl]-2-[(2S,4S)-2-[2-(1-pyrrolidinylcarbonylmeth yl)cyclopropyl]pyrrolidin-4-yl-thio]-1-carbapen-2-em-3-carboxylic acid(compound 190), (1R,5S,6S)-2-[(2S,4S)-2-[2-(aminocarbonylmethyl)cyclopropyl]pyrrolidin-4-ylthio]-6-[(R)-1-hydroxyethyl]-1-methyl-1-carbapen-2-em-3-carboxylic acid(compound 193), (1R,5S,6S)-6-[(R)-1-hydroxyethyl]-1-methyl-2-[(2S,4S)-2-[2-(N-methylaminocarbonylmethyl)cyclopropyl]pyrrolidin4-ylthio]-1-carbapen-2-em-3-carboxylic acid(compound 194), (1R,5S,6S)-2-[(2S,4S)-2-[2-(N,N-dimethylaminocarbonylmethyl)cyclopropyl]0 pyrrolidin-4-ylthio]-6-[(R)-1-hydroxyethyl]-1-methyl-1-carbapen-2-em-3-carboxylic acid(compound 195), (1R,5S,6S)-6-[(R)-1-hydroxyethyl]-1-methyl-2-[(2S,4S)-2-[2-(1-pyrrolidinylcarbonylmethyl)cyclopropyl]pyrrolidin-4-ylthio]-1-carbapen-2-em-3-carboxylic acid(compound 197), (5R,6S)-2-[(2S,4S)-2-[1-(aminocarbonylmethyl(-cyclo propyl]pyrrolidin-4-ylthio]-6-[(R)-1-hydroxyethyl]-1-carbapen-2-em-3-carboxylic acid(compound 200), (5R,6S)-6-[(R)-1-hydroxyethyl]-2-[(2S,4S)-2-[1-(N-methylaminocarbonylmethyl) cyclopropyl]pyrrolidin-4-yl-thio]-1-carbapen-2-em-3-carboxylic acid(compound 201), (5R,6S)-2-[(2S,4S)-2-[1-(N,N-dimethylaminocarbonyl methyl)cyclopropyl]pyrrolidin-4-ylthio]-6-[(R)-1-hydroxyethyl]-1-carbapen-2-em-3-carboxylic acid (compound 202), (5R,6S)-6-[(R)-1-hydroxyethyl]-2-[(2S,4S)-2-[1-(1-pyrrolidinylcarbonyl methyl)cyclopropyl]pyrrolidin-4-yl-thio]-1-carbapen-2-em-3-carboxylic acid(compound 204), (1R,5S,6S)-2-[(2S,4S)-2-[1-(aminocarbonylmethyl)]cyclopropyl]pyrrolidin-4-ylthio]-6-[(R)-1-hydroxyethyl]-1-methyl-1-carbapen-2-em-3-carboxylic acid(compound 207), (1R,5S,6S)-6-[(R)-1-hydroxyethyl]-1-methyl-2-[(2S,4S)-2-[1-(N-methylaminocarbonylmethyl)cyclopropyl]pyrrolidin-4-ylthio]-1-carbapen-2-em-3-carboxylic acid(compound 208), (1R,5S,6S)-2-[(2S,4S)-2-[1-(N,N-dimethylaminocarbonylmethyl)cyclopropyl]pyrrolidin-4-ylthio]-6-[(R)-1-hydroxyethyl]-1-methyl-1-carbapen-2-em-3-carboxylic acid(compound 209), (1R,5S,6S)-6-[(R)-1-hydroxyethyl]-1-methyl-2-[(2S,4S)-2-[1-(1-pyrrolidinylcarbonylmethyl)cyclopropyl]pyrrolidin-4-ylthio]-1-carbapen-2-em-3-carboxylic acid (compound 211), (5R,6S)-2-[(2S,4S)-2-[2-(2-aminocarbonylethyl)-cyclopropyl] pyrrolidin-4-ylthio]-6-[(R)-1-hydroxyethyl]-1-carbapen-2-em-3-carboxylic acid(compound 214), (5R,6S)-6-[(R)-1-hydroxyethyl]-2-[(2S,4S)-2-[2-(2-N-methylaminocarbonyl ethyl)cyclopropyl]pyrrolidin-4-yl-thio]-1-carbapen-2-em-3-carboxylic acid(compound 215), (5R,6S)-2-[(2S,4S)-2-[2-(2-N,N-dimethylaminocarbonylethyl)cyclopropyl]pyrrolidin-4-ylthio]-6-[(R)-1-hydroxyethyl]-1-carbapen-2-em-3-carboxylic acid(compound 216), (5R,6S)-6-[(R)-1-hydroxyethyl]-2-[(2S,4S)-2-[2-(1-pyrrolidinylcarbonyl) ethyl]cyclopropyl]pyrrolidin-4-yl-thio]-1-carbapen-2-em-3-carboxylic acid(compound 218), (1R,5S,6S)-2-[(2S,4S)-2-[2-(2-aminocarbonylethyl) propyl]cyclopropyl]pyrrolidin-4-ylthio]-6-[(R)-1-hydroxyethyl]-1-methyl-1-carbapen-2-em-3-carboxylic acid(compound 221), (1R,5S,6S)-6-[(R)-1-hydroxyethyl]-1-methyl-2-[(2S,4S)-2-[2-(2-N-methylaminocarbonylethyl)cyclopropyl]pyrrolidin-4-ylthio]-1-carbapen-2-em-3-carboxylic acid(compound 222), (1R,5S,6S)-2-[(2S,4S)-2-[2-(2-N,N-dimethylaminocarbonylethyl)cyclopropyl]pyrrolidin-4-ylthio]-6-[(R)-1-hydroxyethyl]-1-methyl-1-carbapen- 2-em-3-carboxylic acid(compound 223), (1R,5S,6S)-6-[(R)-1-hydroxyethyl]-1-methyl-2-[(2S,4S)-2-[2-[2-(1-pyrrolidinylcarbonyl)ethyl]cyclopropyl]pyrrolidin-4-ylthio]-1-carbapen-2-em-3-carboxylic acid (compound 225), (5R,6S)-2-[(2S,4S)-2-[1-(2-aminocarbonylethyl)-cyclopropyl]pyrrolidin-4-ylthio]-6-[(R)-1-hydroxyethyl]-1-carbapen-2-em-3-carboxylic acid(compound 228), (5R,6S)-6-[(R)-1-hydroxyethyl]-2-[(2S,4S)-2-[1-(2-N-methylaminocarbonyl ethyl)cyclopropyl]pyrrolidin-4-yl-thio]-1-carbapen-2-em-3-carboxylic acid(compound 229), (5R,6S)-2-[(2S,4S)-2-[1-(2-N,N-dimethylaminocarbonylethyl) cyclopropyl]pyrrolidin-4-ylthio]-6-[(R)-1-hydroxyethyl]-1-carbapen-2-em-3-carboxylic acid(compound 230), (1R,5S,6S)-2-[(2S,4S)-2-[1-(2-aminocarbonylethyl)cyclopropyl]pyrrolidin-4-ylthio]-6-[(R)-1-hydroxyethyl]-1-methyl-1-carbapen-2-em-3-carboxylic acid(compound 236), (1R,5S,6S)-6-[(R)-1-hydroxyethyl]-1-methyl-2-[(2S,4S)-2-[1-(2-N-methylaminocarbonylethyl)cyclopropyl]pyrrolidin-4-ylthio]-1-carbapen-2-em-3-carboxylic acid(compound 237), (1R,5S,6S)-2-[(2S,4S)-2-[1-(2-N,N-dimethylaminocarbonylethyl)cyclopropyl]pyrrolidin-4-ylthio]-6-[(R)-1-hydroxyethyl]-1-methyl-1-carbapen-2-em-3-carboxylic acid(compound 238), (1R,5S,6S)-6-[(R)-1-hydroxyethyl]-1-methyl-2-[(2S,4S)-2-[1-[2 (1-pyrrolidinylcarbonyl)ethyl]cyclopropyl]pyrrolidin-4-ylthio]-1-carbapen-2-em-3-carboxylic acid (compound 240), (5R,6S)-2-[(2S,4S)-2-[2-(3-aminocarbonylpropyl)cyclopropyl]pyrrolidin-4-ylthio]-6-[(R)-1-hydroxyethyl]-1-carbapen-2-em-3-carboxylic acid(compound 243), (5R,6S)-6-[(R)-1-hydroxyethyl]-2-[(2S,4S)-2-[2-(3-N-methylaminocarbonyl propyl)cyclopropyl]pyrrolidin-4-yl-thio]-1-carbapen-2-em-3-carboxylic acid(compound 244), (5R,6S)-2-[(2S,4S)-2-[2-(3-N,N-dimethylaminocarbonylpropyl)cyclopropyl]pyrrolidin-4-ylthio]-6-[(R)-1-hydroxyethyl]-1-carbapen-2-em-3-carboxylic acid (compound 245), (5R,6S)-6-[(R)-1-hydroxyethyl]-2-[(2S,4S)-2-[2-[3-(1-pyrrolidinyl carbonyl)-propyl]cyclopropyl]pyrrolidin-4-yl-thio]-1-carbapen-2-em-3-carboxylic acid(compound 247), (1R,5S,6S)-2-[(2S,4S)-2-[2-(3-aminocarbonylpropyl)cyclopropyl]-pyrrolidin-4-ylthio]-6-[(R)-1-hydroxyethyl]-1-methyl-1-carbapen-2-em-3-carboxylic acid(compound 250), (1R,5S,6S)-6-[(R)-1-hydroxyethyl]-1-methyl-2-[(2S,4S)-2-[2-(3-N-methylaminocarbonylpropyl)cyclopropyl]-pyrrolidin-4-ylthio]-1-carbapen-2-em-3-carboxylic acid (compound 251), (1R,5S,6S)-2-[(2S,4S)-2-[2-(3-N,N-dimethylaminocarbonylpropyl) cyclopropyl]pyrrolidin-4-ylthio]-6-[(R)-1-hydroxyethyl]1-methyl-1 carbapen-2-em-3-carboxylic acid(compound 252), (1R,5S,6S)-6-[(R)-1-hydroxyethyl]-1-methyl-2-[(2S,4S)-2-[2-[3-(1-pyrrolidinylcarbonyl)propyl]cyclopropyl]pyrrolidin-4-ylthio] -1-carbapen-2-em-3-carboxylic acid (compound 254), (5R,6S)-2-[(2S,4S)-2-[1-(3-aminocarbonylpropyl)cyclopropyl]pyrrolidin-4-ylthio]-6-[(R)-1-hydroxyethyl]-1-carbapen-2-em-3-carboxylic acid(compound 257), (5R,6S)-6-[(R)-1-hydroxyethyl]-2-[(2S,4S)-2-[1-(3-N-methylamino carbonylpropyl)cyclopropyl]-pyrrolidin-4-yl-thio]-1-carbapen-2-em-3-carboxylic acid(compound 258), (5R,6S)-2-[(2S,4S)-2-[1-(3-N,N-dimethylaminocarbonylpropyl) cyclopropyl]pyrrolidin-4-ylthio]-6-[(R)-1-hydroxyethyl]-1-carbapen-2-em-3-carboxylic acid (compound 259), (5R,6S)-6-[(R)-1-hydroxyethyl]-2-[(2S,4S)-2-[1-[3-(1-pyrrolidinyl carbonyl)propyl]cyclopropyl]pyrrolidin-4-yl-thio]-1-carbapen-2-em-3-carboxylic acid(compound 261), (1R,5S,6S)-2-[(2S,4S)-2-[1-(3-aminocarbonylpropyl)cyclopropyl]pyrrolidin-4-ylthio]-6-[(R)-1-hydroxyethyl]-1-methyl-1-carbapen-2-em-3-carboxylic acid(compound 264), (1R,5S,6S)-6-[(R)-1-hydroxyethyl]-1-methyl-2-[(2S,4S)-2-[1-(3-N-methylaminocarbonylpropyl)-cyclopropyl]pyrrolidin-4-ylthio]-1-carbapen-2-em-3-carboxylic acid (compound 265), (1R,5S,6S)-2-[(2S,4S)-2-[1-(3-N,N-dimethylaminocarbonylpropyl) cyclopropyl]pyrrolidin-4-ylthio]-6-[(R)-1-hydroxyethyl]-1-methyl-1-carbapen-2-em-3-carboxylic acid(compound 266) and (1R,5S,6S)-6-[(R)-1-hydroxyethyl]-1-methyl-2-[(2S,4S)-2-[1-[3-(1-pyrrolidinylcarbonyl)-propyl]cyclopropyl]pyrrolidin-4-ylthio]-1-carbapen-2-em-3-carboxylic acid (compound 268).

Among the compounds of the formula (I) and among the specific examples of the compound of the formula (I), more preferred are a group of compounds represented by the formula (I-r):

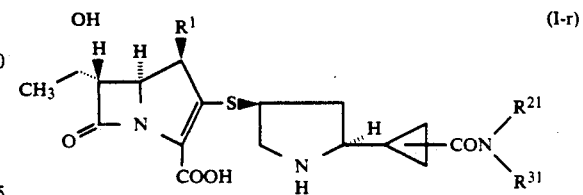

wherein $R^1$ is as defined above, and each of $R^{21}$ and $R^{31}$ which may be the same or different, is a hydrogen atom or a lower alkyl group.

The compound of the formula (I) can be formed into a pharmaceutically acceptable salt or ester by a conventional method.

The salt of the compound of the formula (I) means a common pharmaceutically acceptable salt and includes a salt at the carboxyl group at the 3-position of the carbapenem structure or at the nitrogen atom capable of forming a salt on the pyrrolidine ring at the 2-position of the carbapenem structure.

The basic addition salt at said carboxyl group includes, for example, an alkali metal salt such as a sodium salt or a potassium salt; an alkaline earth metal salt such as a calcium salt or a magnesium salt; an ammonium salt; an aliphatic amine salt such as a trimethylamine salt, a triethylamine salt, a dicyclohexylamine salt, an ethanolamine salt, a diethanolamine salt, a triethanolamine salt or a procaine salt; an aralkylamine salt such as an N,N'dibenzylethylenediamine salt; an aromatic heterocyclic amine salt such as a pyridine salt, a picoline salt, a quinoline salt or an isoquinoline salt; a quaternary ammonium salt such as a tetramethylammonium salt, a tetraethylammonium salt, a benzyltrimethylammonium salt, a benzyltriethylammonium salt, a benzyltributylammonium salt, a methyltrioctylammonium salt or a tetrabutylammonium salt; and a basic amino acid salt such as an arginine salt or a lysine salt.

The acid addition salt at the pyrrolidine base includes, for example, an inorganic salt such as a hydrochloride, a sulfate, a nitrate, a phosphate, a carbonate, a hydrogencarbonate or a perchlorate; an organic salt such as an acetate, a propionate, a lactate, a maleate, a fumarate, a tartrate, a malate, a succinate or an ascorbate; a sulfonate such as a methanesulfonate, an isethionate, a benzenesulfonate or a p-toluenesulfonate; and an acidic amino acid salt such as an aspartate or a glutamate.

The non-toxic ester of the compound of the formula (I) means a common pharmaceutically acceptable ester at the carboxyl group at the 3-position of the carbapenem structure. For example, it includes an ester with an alkanoyloxymethyl group such as an acetoxymethyl group or a pivaloyloxymethyl group, an ester with an alkoxycarbonyloxyalkyl group such as a 1-(ethoxycarbonyloxy)ethyl group, an ester with a phthalidyl group and an ester with a (5-substituted-2-oxo-1,3-cioxol-4-yl)methyl group such as a (5-methyl-2-oxo-1,3-dioxol-4-yl)methyl group.

Now, the process for producing the compound of the present invention will be described. The compound of the formula (I) can be prepared by reacting a compound of the formula (II) as defined above or its reactive derivative with a compound of the formula (III) as defined above to form a compound of the formula (IV) as defined above and if necessary, removing any protective group of the compound of the formula (IV):

The reaction of the compound of the formula (II) with the compound of the formula (III) is preferably conducted by using as the compound of the formula (II) a reactive derivative thereof. Namely, the compound of the formula (II) can be converted to a reactive derivative of the formula:

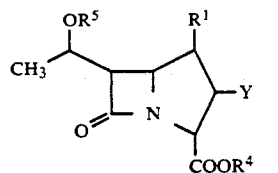

(II')

wherein $R^1$, $R^4$ and $R^5$ are as defined above, and Y is a leaving group, by reacting an activating reagent to the compound of the formula (II) in an inert organic solvent in the presence of a base.

The inert organic solvent to be used for the reaction may, for example, be diethyl ether, tetrahydrofuran, dioxane, benzene, toluene, chlorobenzene, methylene chloride, chloroform, carbon tetrachloride, dichloroethane, trichloroethylene, acetone, ethyl acetate, acetonitrile, N,N-dimethylformamide, hexamethylphosphoric triamide or a mixture of such solvents. Particularly preferred are acetonitrile and benzene.

The base to be used for the reaction may, for example, be a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) or 1,5-diazabicyclo[4.3.0]non-5-ene (DBN); or an aromatic amine such as pyridine, 4-dimethylaminopyridine, picoline, lutidine, quinoline or isoquinoline. Particularly preferred are N,N-diisopropylethylamine and triethylamine.

The activating reagent to be used for the reaction may, for example, be an acid anhydride such as trifluoroacetic anhydride, methanesulfonic anhydride, trifluoromethanesulfonic anhydride or p-toluenesulfonic anhydride; or an acid chloride such as methanesulfonyl chloride, p-toluenesulfonyl chloride or diphenyl chlorophosphate. Particularly preferred is diphenyl chlorophosphate.

In the formula (II'), Y is a leaving group such as a trifluoroacetoxy group, a methanesulfonyloxy group, a trifluoromethanesulfonyloxy group, a p-toluenesulfonyloxy group or a diphenoxyphosphoryloxy group. Particularly preferred is a diphenoxyphosphoryloxy group.

For the reaction, from 1 to 3 mols, preferably from 1 to 1.5 mols of the base and from 1 to 1.2 mols of the activating reagent are used per mol of the compound of the formula (II).

The reaction is conducted usually within a temperature range of from $-40°$ to $50°$ C., preferably from $-20°$ to $20°$ C. and usually completed quantitatively in from 0.5 to 3 hours.

After completion of the reaction, the reaction product is treated in accordance with a usual method to obtain the reactive derivative (II') of the compound of the formula (II) quantitatively.

The compound of the formula (II') may be reacted with the compound of the formula (III) without or after being isolated. The reaction is conducted using the abovementioned inert organic solvent and the base, and from 1 to 2 mols, preferably from 1 to 1.5 mols, of the base and from 1 to 1.2 mols of the compound of the formula (III) are used per mol of the compound of the formula (II'). The reaction is conducted usually within a temperature range of from $-40°$ to $50°$ C., preferably from $-20°$ to $20°$ C. and usually completed quantitatively in from 0.5 to 3 hours.

Further, the compound of the formula (IV) can be prepared in one step from the compound of the formula (II). Namely, without isolating the reactive derivative of the formula (II') prepared from the compound of the formula (II), the compound of the formula (III) is reacted thereto in the same reaction system to prepare the compound of the formula (IV) efficiently. To conduct the production in one step, from 2 to 4 mols, preferably from 2.5 to 3.5 mols, of the base is employed per mol of the compound of the formula (II).

After completion of the reaction, usual treatment is conducted to obtain a crude product of the formula (IV), which may be subjected to a reaction for removing a protecting group without purification. However, it is preferred to purify the crude product (IV) by crystallization or by column chromatography by means of e.g. silica gel.

From the compound of the formula (IV) thus obtained, compound of the formula (I) can be obtained, if necessary, by conducting a reaction for removing a protecting group for a hydroxyl group, an amino or imino group and a carboxyl group.

For the removal of the protecting groups, the method varies depending upon the type of the protecting groups. However, the removal can be conducted in accordance with conventional methods, for example, by solvolysis, by chemical reduction or by hydrogenation.

For example, when in the above formula (IV), the protecting group for the hydroxyl group and/or for the amino or imino group is an aralkyloxycarbonyl group such as a benzyloxycarbonyl group or a p-nitrobenzyloxycarbonyl group, and the protecting group for the carboxyl group is an aralkyl group such as a benzyl group, a p-nitrobenzyl group or a benzhydryl group, such protecting groups can be removed by catalytic hydrogenation by means of a platinum catalyst such as platinum oxide, platinum wire or platinum black, or a palladium catalyst such as palladium black, palladium oxide, palladium-carbon or palladium hydroxide-carbon.

As a solvent to be used for such a catalytic hydrogenation reaction, methanol, ethanol, tetrahydrofuran, dioxane, acetic acid or a solvent mixture of such an organic solvent with water or with a buffer solution of e.g. a phosphate, may be used.

The reaction can be completed in from 0.5 to 4 hours at a temperature within a range of from 0° to 50° C. under hydrogen gas stream of from 1 to 4 atm.

When in the above formula (IV), the protecting group for the hydroxyl group and/or the amino or imino group is an allyloxycarbonyl group, and the protecting group for the carbonyl group is an allyl group, such protecting groups can be removed by reacting an organo-soluble palladium complex catalyst in an inert organic solvent containing an allyl group-capturing agent (method by W. McCombie et al., J. Org. Chem., vol. 47, p. 587–590 (1982)).

The solvent useful for the reaction includes, for example, acetone, diethyl ether, tetrahydrofuran, dioxane, ethyl acetate, acetonitrile, methylene chloride, chloroform and a solvent mixture thereof.

The soluble palladium complex catalyst may, for example, be tetrakis(triphenylphosphine)palladium.

The allyl group-capturing agent may, for example, be sodium 2-ethylhexanoate, potassium 2-ethylhexanoate, pyrrolidine, piperidine and tributyltin hydride.

The reaction is conducted usually within a temperature range of from −10° to 50° C., preferably from 0° to 30° C. using from 0.01 to 0.5 mol of the catalyst and from 1 to 6 mols of the nucleophilic agent relative to 1 mol of the compound of the formula (IV), and the reaction is completed usually in from 0.5 to 3 hours.

Further, when in the above formula (IV), the protecting group for the hydroxyl group and/or the amino or imino group is an o-nitrobenzyloxycarbonyl group, and the protecting group for the carboxyl group is an onitrobenzyl group, such protecting groups can be removed by a photo reaction (method by Amit et al., J. Org. Chem., vol. 39, p. 192–196 (1974)).

After completion of the reactions for removing the protecting groups, the compound of the formula (I) can be isolated by usual treatment such as column chromatography using silica gel or adsorptive resin, freeze-drying or crystallization.

Further, when the protecting group for the carboxyl group at the 3-position of the compound of the formula (IV) is a lower alkanoyloxyalkyl group such as an acetoxymethyl group or a pivaloyloxymethyl group, a methoxymethyl group, an indanyl group, or a phthalidyl group, such an ester will be physiologically hydrolyzed in vivo. Therefore, such a compound can directly be administered to a human being or to an animal without preliminarily removing the protecting group.

The starting material of the formula (II) can be prepared, for example, by a method by Salzmann et al. when $R^1$ is a hydrogen atom (J. Am. Chem. Soc., vol. 102, p.6161–6163 (1981)) or by a method by Shih et al. when $R^1$ is a methyl group (Heterocycles, vol. 21, p.29–40 (1984)).

The compound of the formula (III) as the starting material, can be synthesized-from hydroxyproline via a compound 11.

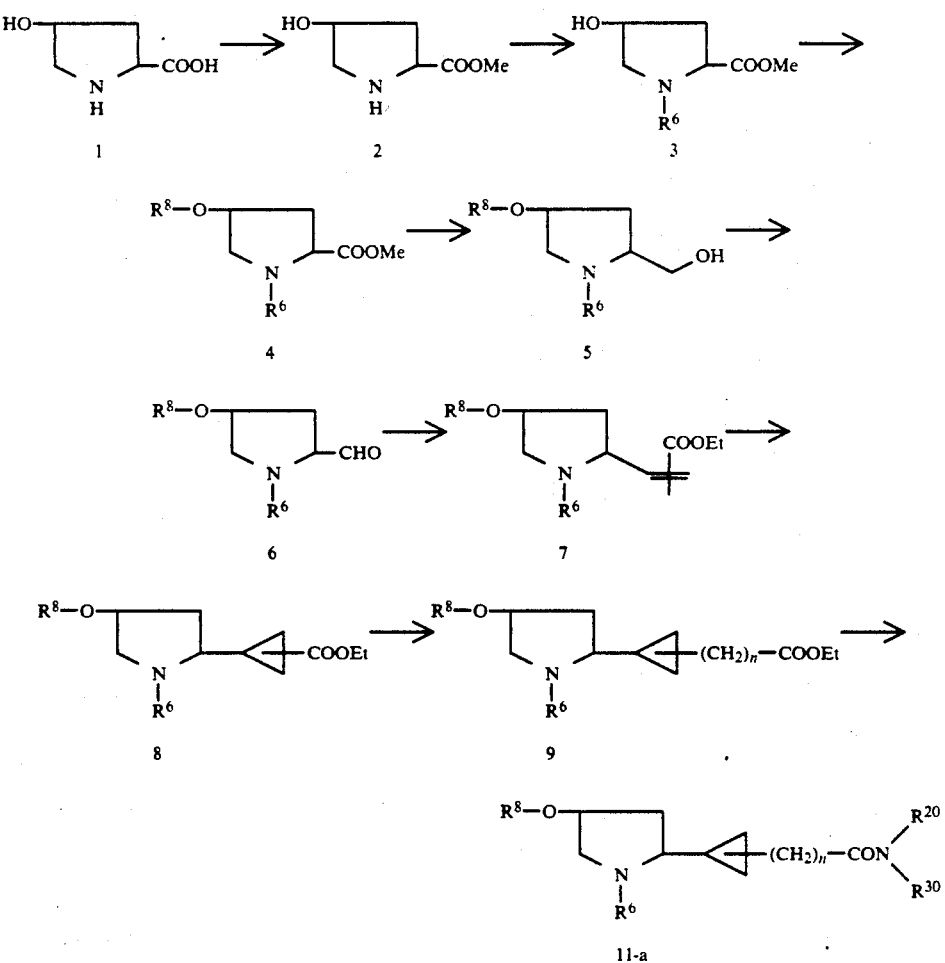

11-a

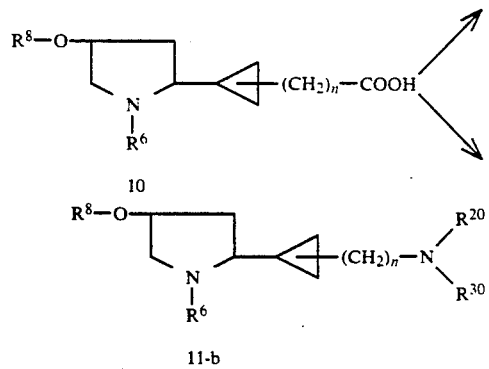

10

11-b

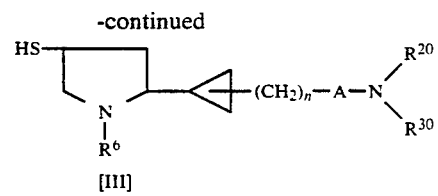

[III]

In the above formulas, $R^6$, $R^{20}$ and $R^{30}$ are as defined above, and $R^8$ is a hydroxyl-protecting group. In accordance with the method of J. Med. Chem., vol. 31, p. 875 (1988), ditto, Vol. 31, p. 1598 (1988), a compound 5 was obtained from a compound 1. Then, by the oxidation reaction as disclosed in e.g. Tetrahedron, vol. 34, p. 1651 (1981), Synthesis, p. 165 (1981), it was converted to a 2-formyl compound 6. The compound 6 was converted to an aquatic acid derivative 7 by a Wittig reaction as disclosed in e.g. Org. React., vol. 14, p. 270 (1965), Helv. Chim. Acta, vol. 62, p. 2091 (1979), Tetrahedron Lett., vol. 24, p. 4405 (1983). Then, it was converted to a cyclopropanecarboxylic acid ester derivative 8 by reacting palladium (II) acetate-diazomethane thereto. Then, the compound 8 was optionally subjected to a chain elongation reaction n times (n=0–3) by a usual method to obtain a ester 9, which was further converted to a carboxylic acid derivative 10 by alkali hydrolysis. The compound 10 was converted to an acid chloride by a usual method, and then an amine was reacted thereto to obtain an amide derivative 11-a. Further the compound 10 was subjected to Crutius reaction to obtain a compound 11-b in e.g. Org. React., vol. 3, p. 337 (1946), J. Org. Chem., vol. 26, p. 3511 (1961).

In the above formulas, $R^6$, $R^8$, $R^{20}$ and $R^{30}$ are as defined above.

Then, from the compound 11, a magnetic derivative of the formula (IIIb) can be obtained by sequentially conducting the protection of amino group, removal of the hydroxyl-protecting group and mesylation of the resulting hydroxyl group (compound 12), acetylthio modification by means of a thioacetate (compound 13) and alkali hydrolysis. The chain elongation reaction is conducted by the following manner.

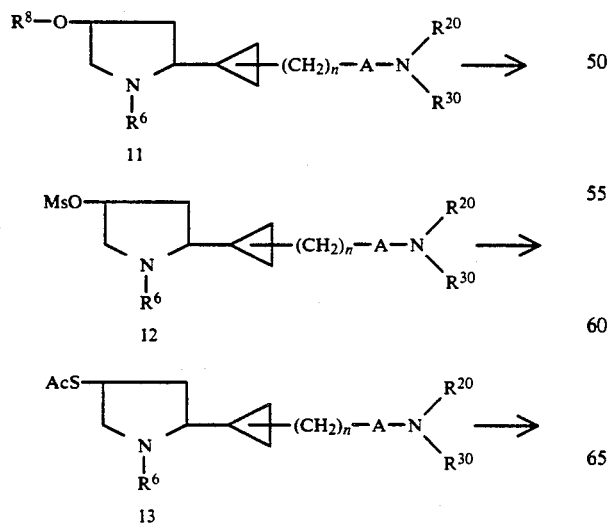

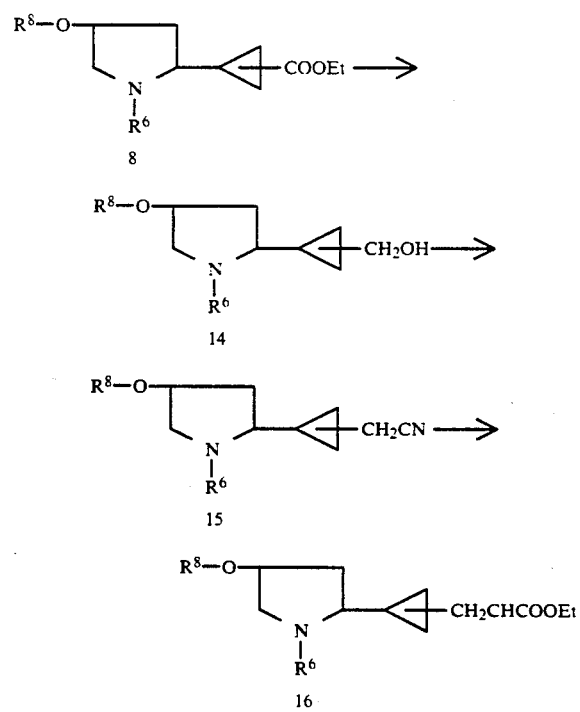

The ester group of a compound 8 is reduced by a usual method to obtain an alcohol 14 (Org. React., vol. 6, p. 469 (1951), J. Org. Chem., vol. 24, p. 627 (1959). This compound 14 is converted to a sulfonic acid ester or a halide, then to a cyanide compound 15 (Synth. Commu. vol. 2, p. 125 (1972). The compound 15 is treated with an alcohol in the presence of hydrochloric acid to afford 16. The carbulation reaction is to be repeated one or two times if it requires.

The compounds of the present invention exhibit strong antibacterial activities against various gram positive bacteria and gram negative bacteria.

To demonstrate the usefulness of the compounds of the present invention, the in vitro antibacterial activities against bacteria were measured by the following agar plate dilution method (standard method by Japan Chemotherapy Society, Chemotherapy, vol. 29, p. 76-79 (1981)). One platinum loopful of each test microorganism incubated overnight in Mueller Hinton broth, was inoculated to Mueller Hinton agara (inoculum size: $10^6$ CFU/ml). Such culture media contained antibacterial agents in various concentrations. After incubation at 37° C. for 16 hours, the minimum inhibitory concentrations (MIC: μg/ml) were measured.

The results of the antibacterial activities of the compounds of the present invention are shown in the following Tables.

TABLE 1

| MIC (μg/ml, $10^6$ CFU/ml) | |
|---|---|
| Test microorganism | Compound of Example 6 |
| S. aureus 209P NIHJ JC1 | 0.025 |
| S. aureus MB4970 | 0.05 |
| S. aureus JS1* | 0.78 |

*β-lactamase producing microorganism

The compounds of the present invention show strong antibacterial activities against various gram positive bacteria and gram negative bacteria. As representative examples, the antibacterial activities of the compounds of the present invention described in the Examples, were measured by a disc diffusion test by the method of Bauer et al. (Amer. J. Clin. Pathol., vol. 45, p. 493 (1966)). Thienamycin or imipenem was used as the internal standard.

MIC of each test compound was calculated from the diameter of the inhibition ring formed by the disc containing the test compound by using the calculation formula reported by Humphrey and Lightbown (J. Gen. Microbiol., vol. 7, p. 129 (1952)). For each microorganism, a geometrical average of MIC was obtained, and the activity ratio to thienamycin was calculated.

The antibacterial activities are represented by the ratio to thienamycin (=1.0), whereby the larger the numerical value, the higher the activities.

The relative antibacterial potency and the DHP-I susceptibility of the compounds of the present invention were compared with imipenem and meropenem. The DHP-I susceptibility was quantitatively analyzed by the method by Kropp et al., Antimicrob.,- Agents Chemother., vol. 22, p. 62-70 (1982), whereby the smaller the numerical value representing the ratio to imipenem (=1.0), the higher the stability. The results are shown in Table 2.

TABLE 2

| Relative antibacterial potency and DHP-I susceptibility | | | | |
|---|---|---|---|---|
| | Example 6 | Example 76 | imipenem | meropenem |
| Meth-R. S. aureus | 5.41 | 16.7 | 2.57 | 3.15 |
| DHP-I | — | 0.08 | 1.0 | 0.12 |

TABLE 2-continued

| Relative antibacterial potency and DHP-I susceptibility | | | | |
|---|---|---|---|---|
| | Example 6 | Example 76 | imipenem | meropenem |
| susceptibility | | | | |

The compounds of the present invention have excellent antibacterial activities against various gram positive bacteria and gram negative bacteria and are useful as antibacterial agents for the treatment and prevention of the human infectious diseases caused by such bacteria. Typical pathogens sensitive to the antibacterial agents of the present invention include, for example, species of genus Staphylococcus, genus Enterococcus, genus Escherichia, genus Enterobacter, genus Klebsiella, genus Serratia, genus Proteus and genus Pseudomonas. The compounds of the present invention exhibit excellent antibacterial activities particularly against Methicillin resistant *Staphylococcus aureus* and against thienamycin resistant *Pseudomonas aeruqinosa*.

The compounds of the present invention are very stable against DHP-I although the stability varies depending upon the individual compounds, and they are excellent also in the physicochemical stability and in the solubility in water.

The compounds of the present invention may be used in the form of drug formulations suitable for non-oral administration, oral administration or external administration, by mixing them with carriers of solid or liquid excipients known in this field. The main administration route is non-oral (intravenous or intramuscular injection) administration by injection or local administration. Drug formulations include liquid formulations such as injection solutions, syrups or emulsions, solid formulations such as tablets, capsules or granules, and external application formulations such as ointments or suppositories. These formulations may contain additives such as a base, an assisting agent, a stabilizer, a wetting agent, an emulsifier, an absorption-promoting agent, a surfactant, etc. which are commonly employed, as the case requires.

The additives include, for example, distilled water for injection, Ringer's solution, glucose, sucrose syrup, gelatin, edible oil, cacao butter, ethylene glycol, sucrose, corn starch, magnesium stearate and talc.

The dose varies depending upon the condition of the patient, the weight, the age, the sex, the type of formulation, the number of administration times, etc. Usually, however, a preferred daily dose of the active ingredient to an adult is from about 5 to 50 mg/kg, and a preferred daily dose to a child is within a range of from about 5 to 25 mg/kg, which is preferably administered once a day or in a few times a day.

The compound of the present invention may be administered in combination with a DHP-I inhibiting agent such as cilastatin [sodium (Z)-7-(L-amino-2-carboxyethylthio) -2-(2,2-dimethylcyclopropanecarboxamide) -2-heptenoate](Japanese Unexamined Patent Publication No. 81518/1981; European Patent No. 28,778; J. Med. Chem., vol. 30, p. 1074 (1987)).

Now, the present invention will be described in further detail with reference to Examples and Reference Examples. However, it should be understood that the present invention is by no means restricted by such specific Examples.

EXAMPLE 1

Sodium (1R,5S,6S)-2-(2S,4S)-2-[trans-2-(N,N-dimethylaminocarbonyl)cyclopropyl]pyrrolidin-4-ylthio]-6-[(R)-1-hydroxyethyl]-1-methyl-1-carbapen-2-em-3-carboxylate

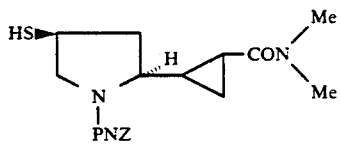
1a)

To a solution of trans-N,N-dimethyl-2-[(2S,4S)-4-acetylthio -N-(4-nitrobenzyloxycarbonyl)pyrrolidin-2-yl]cyclopropanecarboxamide (220 mg, 0.5 mmol) in methanol (11 ml) was added 2N sodium hydroxide solution(0.50 ml, 1.0 mmol) under ice-cooling, and the solution stirred for 1 hour. To the reaction mixture was added 6N hydrochloric acid (0.17 ml, 1.0 mmol), and the mixture poured into water (10 ml) and extracted with methylene chloride (20 ml×2). The organic layer was dried (MgSO4) and evaporated in reduced pressure to give a residue of trans-N,N-dimethyl-2-[(2S,4S)-4-mercapto-N-(4-nitrobenzyloxycarbonyl) pyrrolidin-2-yl]cyclopropanecarboxamide.

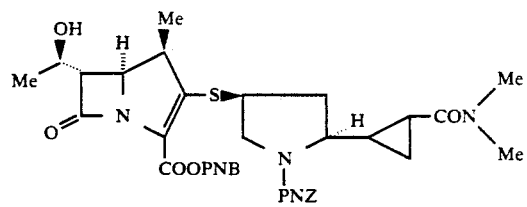
1b)

To a solution of the residue obtained in the previous reaction and 4-nitrobenzyl (1R,5S,6S)-2-diphenoxyphosphoryloxy -6-[(R)-1-hydroxyethyl]-1-methyl-1-carbapen-2-em-3-carboxylate (240 mg, 0.40 mmol) in acetonitrile (12 ml) was added N,N-diisopropylethylamine (84 µl, 0.48 mmol) dropwise. After being stirred for 1 hour at room temperature, the reaction mixture was poured into saturated aqueous sodium bicarbonate (20 ml), and extracted with ethyl acetate (30 ml×2). The organic layer was dried (MgSO4) and evaporated, the residue subjected to column chromatography on silica gel (Wakogel ® C-300, elution with 5% methanol in ethyl acetate) to give 4-nitrobenzyl (1R,5S,6S)-2-[(2S,4S)-2-[trans -2-(N,N-dimethylaminocarbonyl)cyclopropyl]-N-(4-nitrobenzyloxycarbonyl) pyrrolidin-4-ylthio]-6-[(R)-1-hydroxyethyl]-1-methyl-1-carbapen-2-em-3-carboxylate (243 mg, 82% yield from enolphosphate).

NMR(CDCl3) δ:
1.28(3H,d,J=8Hz),1.38(3H,d,J=8Hz),2.90 and 2.98(3H, each s),3.12(3H,br s),5.24(2H,br s),4.40(2H,ABq,$J_{AB}$=16Hz,$\Delta \geq _{AB}$32 52Hz),7.50(2H,d,J=8Hz),7.51(2H,d,J=8Hz), 8 24(2H,d,J=8Hz),8.25(2H,d,J=8Hz).

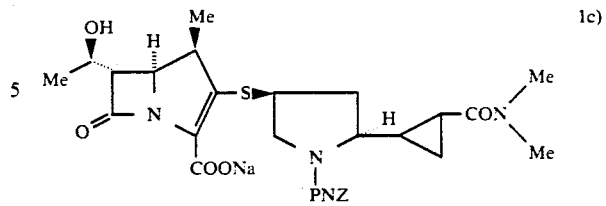
1c)

A solution of the compound (240 mg, 0.32 mmol) obtained in the previous reaction in tetrahydrofuran (THF) (18 ml), 0.1M sodium 3-(morpholino)-propanesulfonate's buffer (pH7.0, 18 ml), and ethanol (1.8 ml) was subjected to hydrogenolysis at 1 atmosphere of hydrogen using 10% palladium-carbon for 1 hour (240 mg, treated under hydrogen atmosphere in ethanol for 1 hour before use). After the catalyst was removed by filtration, the filtrate washed with ethyl acetate (20 ml) and concentrated in reduced pressure. The residue containing two diastereomer isomeres was subjected to ODS reverse phase column chromatography (YMC·GEL ® ODS-AQ 120-Sa50, elution with 30% methanol). The fractions containing the desired product were concentrated, and then lyophilized to give the title compound diastereomer A (22 mg, 41% yield), the diastereomer B(the less -polar compound, 23 mg, 17% yield), and a mixture of the diastereomer isomers (20 mg, 14% yield).

Diastereomer A

NMR(D2O) δ:
1.14(3H,d,J=8Hz),1.20(3H,d,J=8Hz),2.88(3H,s),3.12(-3H, s).

HPLC: Column:YMC ®-Pack ODS-A,5 µ,4.6φ×150mm. Eluent:0.01M Phosphate buffer(pH6.5)/MeOH(90/10). Flow rate: 0.8 ml/min. Column temperature: 40° C. Detector: UV 290nm. Retention time: 6.6 min.

Diastereomer B

NMR(D2O) δ:
1.12(3H,d,J=8Hz),1.18(3H,d,J=8Hz),2.88(3H,s),3.14(-3H, s).

HPLC(the same condition as the diastereomer A) Retention time: 7.5 min.

EXAMPLE 2

Sodium (1R,5S, 6S)-6-[(R)-1-hydroxyethyl]-1-methyl-2-[(2S,4S)-2-trans-2-(N-methylaminocarbonyl)cyclopropyl]pyrrolidin-4-ylthio]-1-carbapen-2-em-3-carboxylate

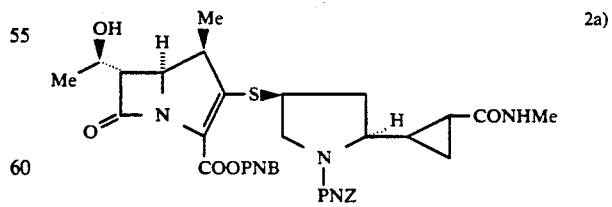
2a)

The same procedure as in EXAMPLE 1a and 1b was carried out by using trans-2-[(2S,4S)-4-acetylthio-N-(4-nitrobenzyloxycarbonyl) pyrrolidin-2-yl]-N-methylcyclopropanecarboxamide (180 mg, 0.42 mmol)and 4-nitrobenzyl (1R,5S,6S)-2-diphenoxyphosphoryloxy-6-[(R)-1-hydroxyethyl]-1-methyl-1-carbapen-2-em-3-carboxylate(203 mg, 0.34 mmol) to give 4-nitrobenzyl (1R,5S,6S)-6-[(R)-1-hydroxyethyl]-1-methyl-2-[(2S,4S)-2-[trans-2-(N-methylaminocarbonyl) cyclopropyl]-N-(4-nitrobenzyloxycarbonyl)pyrrolidin-4-ylthio]-1-carbapen-2-em-3-carboxylate (340 mg).

NMR(CDCl₃) δ:
1.24(3H,d,J=8Hz),1.36(3H,d,J=8Hz),2.72 and 2.74(3H, each s),2.78and2.80(3H,each s),5.20(2H,br s),5.38 (2H,ABq.J$_{AB}$=12Hz,Δv-$_{AB}$=52Hz),7.64(2H,d,J=8Hz),8.22(4H, d,J=8Hz).

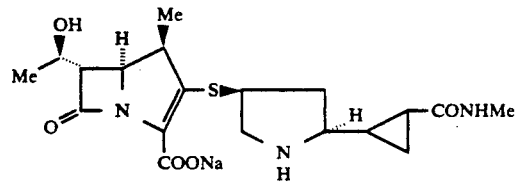

The same procedure as in EXAMPLE 1c was carried out by using the compound (340 mg) obtained in EXAMPLE 2a to give the title compound diastereomer A (16 mg, 8.3% yield) and the diastereomer B (the less polar compound, 36 mg, 18.7% yield).

Diastereomer A

NMR(D₂O)δ:
0.96(1H,m),1.16(3H,d,J=8Hz),1.26(3H,d,J=8Hz),1.50-~1.80(2H,m),2.50~2.80(1H,m),2.70(3H,s),3.00~3.60(-5H, m),3.90(1H,m),4.20(2H,m).

IR(KBr)cm⁻¹: 3400, 1750, 1640, 1620, 1400, 1260, 1100.

HPLC(the same condition as EXAMPLE 1c). Retention time: 4.0 min.

Diastereomer B

NMR(D₂O) δ:
0.96(1H,m),1.16(3H,d,J=8Hz),1.26(3H,d,J=8Hz),1.50-~1.90(2H,m),2.50~2.80(1H,m),2.70(3H,s),3.10~3.80(-5H, m),3.94(1H,m),4.20(2H,m).

IR(KBr)cm⁻¹: 3400,1750,1600,1400,1260,1100.

HPLC(the same condition as EXAMPLE 1c), Retention time: 5.1 min.

EXAMPLE 3

Sodium (1R,5S,6S)-2-[(2S,4S)-2-[trans-2-(aminocarbonyl)cyclopropyl]pyrrolidin-4-ylthio]-6-[(R)-1-hydroxyethyl]-1-methyl-1-carbapen-2-em-3-carboxylate

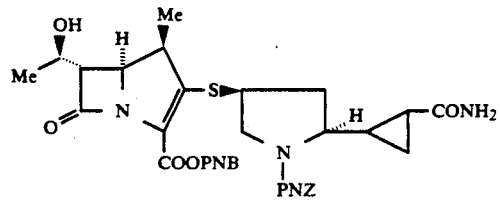

The same procedure described in EXAMPLE 1a and 1b was carried out by using trans-2-[(2S,4S)-4-acetylthio-N-(4-nitrobenzyloxycarbonyl) pyrrolidin-2-yl]cyclopropanecarboxamide (180 mg, 0.44 mmol) and 4-nitrobenzyl (1R,5S,6S)-2-diphenoxyphosphoryloxy-6-[(R)-1-hydroxyethyl]-1-methyl-1-carbapen-2-em-3-carboxylate(184 mg, 0.31 mmol) to give 4-nitrobenzyl (1R,5S,6S)-2-[(2S,4S)-2-[trans-2-(aminocarbonyl)cyclopropyl]pyrrolidin-4-yl-thio]-6-[(R)-1-hydroxyethyl]-1-carbapen-2-em-3-carboxylate(191 mg, 61% yield).

NMR(CDCl₃) δ:
1.24(3H,d,J=8Hz),1.34(3H,d,J=8Hz),5.20(2H,br s),5.36 (2H,ABq.J$_{AB}$=14Hz,Δv-$_{AB}$=50Hz),7.50(2H,d,J=8Hz),7.64(2H, d,J=8Hz),8.20(4H,d,J=8Hz)

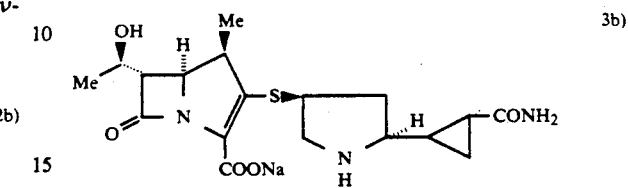

The same procedure as in EXAMPLE 1c was carried out by using the compound (210 mg, 0.30 mmol) obtained in EXAMPLE 3a to give the title compound diastereomer A (25 mg, 21% yield) and the diastereomer B (24 mg, 20% yield).

Diastereomer A

NMR(D₂O) δ:
0.94(1H,m),1.10(3H,d,J=8Hz),1.20(3H,d,J=8Hz),1.50-~1.80(2H,m),2.60(1H,m),3.00~3.60(6H,m),3.86(1H,m-),4.15 (2H,m).

IR(KBr)cm⁻¹: 3400,1750,1660,1600,1400.

HPLC(the same condition as EXAMPLE 1c except eluent), Eluent: 0.01M Phosphate buffer (pH6.5)/MeOH(85/15), Retention time: 5.1 min.

Diasteromer B

NMR(D₂O) δ:
0.96(1H,m),1.12(3H,d,J=8Hz),1.20(3H,d,J=8Hz),1.50-~1.80(2H,m),2.62(1H,m),3.00~3.60(6H,m),3.86(1H,m-),4.16 (2H,m).

IR(KBr)cm⁻¹: 3400,1750,1660,1600,1400.

HPLC(the same condition as the diastereomer A), Retention time: 9.1 min.

EXAMPLE 4

Sodium (5R,6S)-6-[(R)-1-hydroxyethyl]-2-[(2S,4S)-2-[trans-2-(N-methylaminocarbonyl)cyclopropyl]pyrrolidin-4-ylthio]-1-carbapen-2-em-3-carboxylate

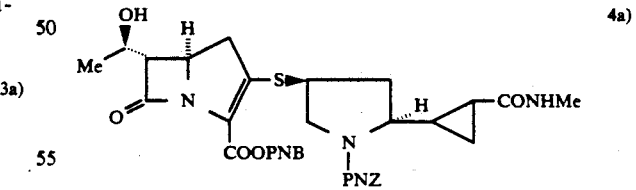

The same procedure described in EXAMPLE 1a and 1b was carried out by using trans-N-methyl-2-[(2S,4S)-4-acetylthio-N-( 4-nitrobenzyloxycarbonyl)pyrrolidin-2-yl]cyclopropanecarboxamide (180 mg, 0.42 mmol) and 4-nitrobenzyl (5R, 6S)-2-diphenoxyphosphoryloxy-6-[(R)-1-hydroxyethyl]-1-carbapen-2-em-3-carboxylate (203 mg, 0.34 mmol) to give 4-nitrobenzyl (5R, 6S)-6-[(R)-1-hydroxyethyl]-2-[(2S,4S)-2-[trans-2-(N-methylaminocarbonyl) cyclopropyl]-N-(4-nitrobenzyloxycarbonyl)pyrrolidin-4-ylthio]-1-carbapen-2-em-3-carboxylate(340 mg).

NMR(CDCl₃) δ: 1.36(3H,d,J=8Hz),2.80 and 2.84(3H,each s),5.24(2H, br s),5.40(2H,ABq,$J_{AB}$=12Hz,$\Delta v_{AB}$=48Hz),7.52(2H,d, J=8Hz),7.66(2H,d,J=8Hz),8.24(2H,d,J=8Hz),8.26(2-H,d, J=8Hz)

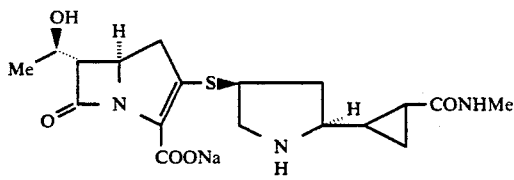

The same procedure described in EXAMPLE 1b and 1c by using the compound (115 mg, 0.16 mmol) obtained in EXAMPLE 4a was carried out to give the title compound (24 mg, 38% yield) as a powder.
NMR(D₂O) δ: 0.90(1H,m),1.20(3H,d,J=8Hz),1.40~1.80(2H,m),2.50-~2.70 (1H,m),2.68(3H,s),2.90~3.60(7H,m),3.80(1H,m),4.16(2-H, m).
IR(KBr)cm⁻¹: 3400,1760,1640,1600,1400,1260.
HPLC (the same condition as EXAMPLE 1c), Retention time: 4.1 min.

EXAMPLE 5

(1R,5S,6S)-2-(2S,4S)-2-2-(Aminocarbonyl)cyclopropyl]pyrrolidin-4-ylthio]-6-[(R)-1-hydroxyethyl]-1-methyl-1-carbapen-2-em-3-carboxylic acid (diastereomer A)

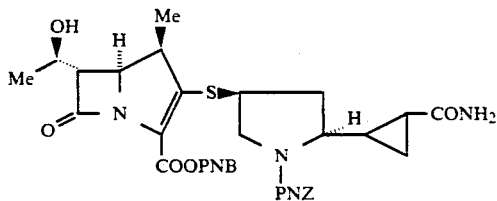

The same procedure described in EXAMPLE 1a and 1b was carried out by using trans-2-[(2S,4S)-4-acetylthio-N-( 4-nitrobenzyloxycarbonyl)pyrrolidin-2-yl]-cyclopropanecarboxamide diastereomer A (1.0 g, 2.46 mmol) obtained in REFERENCE 4 and 4-nitrobenzyl (1R, 5S, 6S)2-diphenoxyphosphoryloxy-6-[(R)-1-hydroxyethyl]-1-methyl-1-carbapen-2-em-3-carboxylate (1.25 g, 2.10 mmol) to give 4-nitrobenzyl (1R, 5S, 6S)-2-[(2S,4S)-2-[trans2-(aminocarbonyl) cyclopropyl]-pyrrolidin-4-ylthio]-6-](R)-1-hydroxyethyl]-I-carbapen-2-em-3-carboxylate diastereomer A (1.32 g, 76% yield).

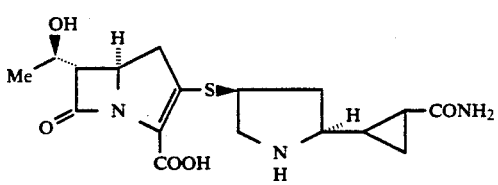

Deprotection reaction of the compound obtained in the previous reaction, followed by ODS reverse phase column chromatography, was carried out according to the same procedure described in EXAMPLE 1c. After the eluent was concentrated to 50 ml, the concentrate adjust to pH5.0 with 0.1M phosphoric acid, and subjected to reverse phase column chromatography (elution with 20% methanol). The fractions containing the desired product ° were concentrated in reduced pressure, and then lyophilized to the title compound (300 mg, 41% yield) as a powder.

After this powder was dissolved in water (0.5 ml), acetone (1.0 ml) added, and the mixture allowed to stand for 1 hour. The crystalline precipitate was collected by filtration and dried to give the title crystalline compound (211 mg).
NMR(D₂O) δ: 1.00(1H,m),1.10(3H,d,J=8Hz),1.20(3H,d,J=8Hz),1.60-~1.85(2H,m),2.70(1H,m),3.20~3.50(5H,m),3.60(1H,m),3.95 (1H,m),4.20(2H,m).
HPLC (the same condition as EXAMPLE 3b), Retention time: 5.1 min.

EXAMPLE 6

(1R, 5S, 6S)-2-[(2S,4S)-2-[2-(Aminocarbonyl)cycropropyl]pyrrolidin-4-ylthio]-6-[(R)-1-hydroxyethyl]-1-methyl-1-carbapen-2-em-3-carboxylic acid

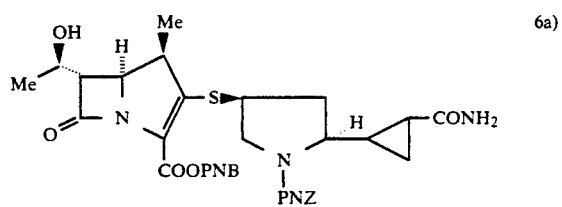

The same procedure described in EXAMPLE 1a and 1b was carried out by using trans-2-[(2S,4S)-4-acetylthio-N-(4-nitrobenzyloxycarbonyl) pyrrolidin-2-yl]cycloropanecaboxamide diastereomer B (529 mg, 1.30 mmol) obtained in REFERENCE 4 and 4-nitrobenzyl (1R, 5S, 6S)-2-diphenoxyphosphoryloxy-6-](R)-1-hydroxyethyl]-1-methyl1-carbapen-2-em-3-carboxylate (672 mg, 1.13 mmol) to give 4-nitrobenzyl (1R, 5S, 6S)-2-](2S,4S)-2-[trans-2-(aminocarbonyl)cyclopropyl]-pyrrolidin-4-ylthio]-6-[(R)-1-hydroxyethyl]-1-carbapen-2-em-3-carboxylate diastereomer B (723 mg, 78% yield).

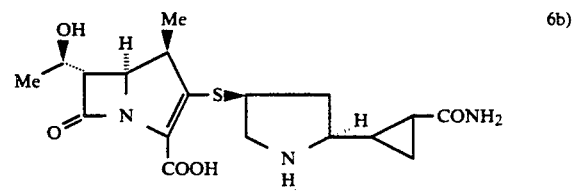

The same procedure described in EXAMPLE 5b was carried out by using the compound (723 mg, 1.02 mmol) obtained in the previous reaction to give the titile compound diasstereomer B (174 mg, 41% yield).
NMR(D₂O) δ: 1.05(1H,m),1.18(3H,d,J=8Hz),1,22(3H,d,J=8Hz),1.60-~2.00(2H,m),2.70(1H,m),3.20~3.50(5H,m),3.60(1H,m),3.95 (1H,m),4.20(2H,m).
HPLC(the same conditions as EXAMPLE 3b). Retention time: 9.1 min.

EXAMPLE 7

(1R,5S,6S)-2-](2S,4S)-2-[trans-2-(Aminomethyl)cyclopropyl]pyrrolidin-4-ylthio]-6-[(R)-1-hydroxyethyl]-1-methyl-1-carbapen-2-em-3-carboxylic acid

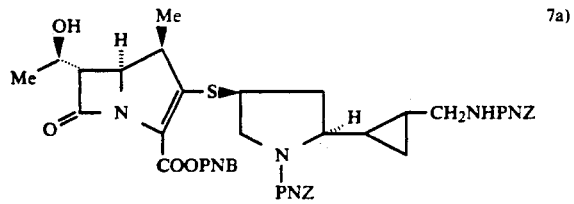
7a)

The same procedure described in EXAMPLE 1a and 1b carried out by using (2S,4S)-4-acetylthio-[trans-2-(4-nitrobenzyloxycarbonylaminomethyl) cyclopropyl]-1-(4-nitrobenzyloxycarbonyl) pyrrolidine (diastereomer A, 232 mg, 0.40 mmol) obtained in REFERENCE 5e and 4-nitrobenzyl (1R, 5S, 6S)-2-diphenoxyphosphoryloxy-6-[(R)-1-hydroxyethyl]-1 methyl-1-carbapen-2-em-3-carboxylate (217 mg, 0.36 mmol) to give 4-nitrobenzyl (1R, 5S, 6S)-6-[(R)-1-hydroxyethyl]-1-methyl-2-[(2S,4S)-2-[trans-2-(4-nitrobenzyloxycarbonylaminomethyl)cyclopropyl]-1-(4-nitrobenzyloxycarbonyl)pyrrolidin-4-ylthio]-1-carbapen-2-em-3-carboxylate diastereomer A (277 mg, 87% yield) from enolphosphate).

NMR(CDCl3) δ:
0.50(2H,m),0.90(2H,m),1.28(3H,d,J=6Hz),1.38(3H,d,J=6Hz),1.80(2H,m),2.50(1H,m),2.80~4:40(9H,m),5.20(-5H,
m),5.52(1H,d,J=14Hz),7.50(4H,d,J=8Hz),7.66(2H,d,J=8Hz),8.24(6H,m).

The diastereomer B (183 mg, 88% yield) was obtained from 4-acetylthiopyrrolidine derivative (151 mg, 0.26 mmol, the compound obtained in REFERENCE 5e) by the same method.

NMR(CDCl3) δ:
0.48(2H,m),0.90(2H,m),1.28(3H,d,J=6Hz),1.38(3H,d,J=6Hz),1.90(2H,m),2.50(1H,m),3.00~4.40(9H,m),5.20(-5H,
m),5.52(1H,d,J=14Hz),7.50(4H,m),7.66(2H,d,J=8Hz),8.20 (6H,m).

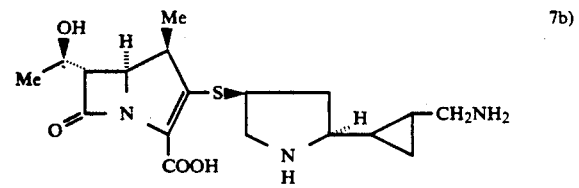
7b)

The same procedure described in EXAMPLE 1c was carried out by using the compound (diastereomer A, 270 mg, 0.31 mmol) obtained in the previous reaction to give the diastereomer A of the title compound (33 mg). HPLC: Column: YMC®-Pack ODS-A,5μ,4.6φ×150mm. Eluent: 0.01M Phosphate buffer (pH5.7)/MeOH(70/30). Flow rate: 0.8 ml/min. Column temperature: 40° C. Detector: UV 290nm. Retention time: 2.51 min.

The diastereomer B of the title compound (16 mg) was obtained from the compound (diastereomer B, 183 mg, 0.21 mmol) obtained in the previous reaction.

HPLC (the same condition as the diastereomer A). Retention time: 3.82 min.

EXAMPLE 8

(1R,5S,6S)-2-[(2S,4S)-2-(trans-2-Aminomcyclopropyl)-pyrrolidin-4-ylthio]-6-[(R)-1-hydroxyethyl]-1-methyl-1-carbapen-2-em-3-carboxylic acid

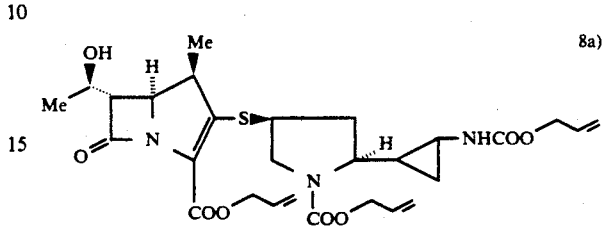
8a)

The same procedure described in EXAMPLE 1a and 1b was carried out by using (2S,4S)-2-(trans-2-allyloxylcarbonyaminocyclopropyl) -4-acetylthio-N-(allyloxycarbonyl)pyrrolidin (232 mg, 0.63 mmol) and allyl (1R, 5S,6S)-2-diphenoxyphosphoryloxy-6-[(R)-1-hydroxyethyl ]1-methyl-1-carbapen-2-em-3-carboxylic acid (352 mg, 0.70 mmol) to give allyl (1R,5S,6S)-6-[(R)-1-hydroxyethyl]-1-methyl-2-[(2S,4S)-2-[trans-2-(allyloxycarbonylamino) cyclopropyl]-1-(allyloxycarbonyl)pyrrolidin-4-ylthio]-1-carbapen-2-em-3-carboxylate (169 mg, 42% yield from enolphosphate)

NMR(CDCl3) δ:
1.24(3H,d,J=6Hz),1.36(3H,d,J=6Hz).

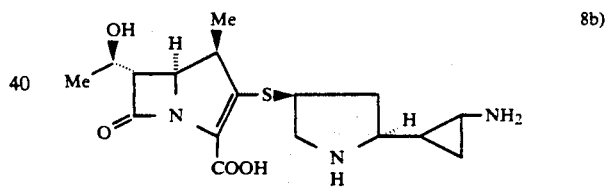
8b)

The compound (169 mg, 0.34 mmol) obtained in the previous reaction was disolved in CH2Cl2 (3.4 ml) and H2O (34 μl). To this solution were added successively bis triphenylphosphin palladium chloride (4.1 mg, 0.0058 mmol) and tributyltin hydride (0.63 ml, 2.35 mmol) under N2 with ice-cooling. Then, this mixture was stirred at room temperature for 1 hour, diluted with CHCl3 (30 ml) and extracted with H2O (15 ml×2). Organic layers were combined and evapolated followed by lyophilization to afford the title compound (76 mg, 70%).

NMR(D2O) δ:
1.14(3H,d,J=6Hz),2.00(3H,d,J=6Hz).

HPLC: Column: YMC®-Pack ODS-A,5μ,4.6φ×150mm. Eluent: 0.01M Phosphate buffer (pH6.5)/MeOH(80/20). Flow rate: 0.8 ml/min. Column temperature: 40° C. Detector: UV 290nm. Retention time: polar isomer 3.20 min.
less polar isomer 5.31 min.

REFERENCE 1 trans-2-(2S,4S)-4-Acetylthio-N-(4-nitrobenzyloxycarbonyl) pyrrolidin-2-yl]-N,N-dimethylcyclopropanecarboxamide

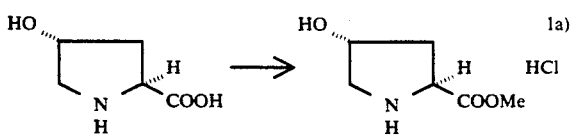
1a)

To a solution of acetyl chloride (19 ml, 270 mmol) in methanol(MeOH) (170 ml) was added L-hydoxyproline (25 g, 190 mmol) at 0° C., and the resulting mixture was heated to reflux with stirring over 7 hours.

After the reaction mixture was cooled to room temperature, diethyl ether (340 ml) was added and stirring of the mixture was continued for an additional 1 hour. The resulting crystal was collected by filtration, washed with a mixture of diethyl ether and MeOH(2:1, 50 ml) and dried under nitrogen atmosphere for 4 hours to give L-hydroxyproline methyl ester hydrochloride (30.64 g, 89% yield).

NMR(DMSO-$d_6$) δ: 2.14(2H,m),3.1(1H,d,J=12Hz),3.4(1H,dd,J=4&12Hz),-3.82 (3H,s),4.48(2H,m),5.66(1H,br s),9.9(2H,br s)

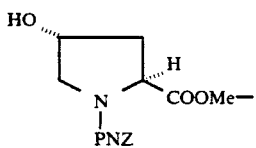
1b)

To a clear solution of L-hydroxyproline methyl ester hydrochloride (27.2 g, 0.15 mol) and triethylamine (50 ml, 0.36 mol) in chloroform (500 ml) was added 4,6-dimethyl-2-(4-nitrobenzyloxycarbonylthio)pyrimidine (40.7 g, 0.13 mol) and then the resulting solution was stirred at room temperature for 12 hours, sequentially washed with $H_2O$ (200 ml), 0.5N NaOH (400 ml) and brine (200 ml) and dried (MgSO$_4$). Concentration followed by silicagel column chromatography (Wakogel® C-300, ethyl acetate) afforded (2S, 4R)-4-hydroxy-N-(4-nitrobenzyloxycarbonyl)proline methyl ester (34.5 g, 70.9% yield) as an oil.

NMR(CDCl$_3$) δ: 1.90~2.45(2H,m),3.60~3.90(2H,m),3.66and3.76(3-H,each s),4.56(1H,m),5.24and5.26(2H,ABq-,$J_{AB}$=12Hz,$\Delta\nu_{AB}$=40Hz and s),7.46and7.52(2H,each d,J=8Hz),8.24(2H,d,J=8Hz).

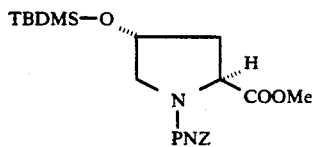
1c)

To a stirred solution of the compound (48.2 g, 0.15 mol) obtained in the previous reaction and imidazole (20.2 g, 0.30 mol) in N,N-dimethylformamide (480 ml) was added tert-butyldimethylsilyl chloride (26.9 g, 0.18 mol) at room temperature. The reaction mixture was stirred for 1.5 hours at the same temperature, poured into saturated aqueous NaHCO$_3$ (200 ml) and extracted with ethyl acetate (500 ml). The organic portion was then dried (MgSO$_4$) and concentrated in vacuo and then subjected to silicagel column chromatography (Wakogel ® C-300, ethyl acetate-hexame 1:3) to afford (2S, 4R)-4-tert-butyldimethylsiloxy-N-(4-nitrobenzyloxycarbonyl) proline methyl ester (61.7 g, 95% yield) as an oil.

NMR(CDCl$_3$) δ: 0.06(6H,s),0.86(9H,s),2.0~2.4(2H,m),3.40~3.80(2H,m-), 3.66 and 3.78(3H,each s),4.46(2H,m),5.20(2H,m),7.50 (2H,m),8.24(2H,d,J=8Hz).

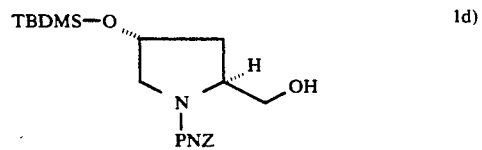
1d)

To a solution of the compound (50.8 g, 0.11 mol) obtained in the above reaction in THF (508 ml) were added NaBH$_4$ (10.5 g, 0.28 mol) and LiCl (11.7 g, 0.28 mol), and then stirring was continued for 30 minutes at room temperature. After addition of EtOH (1.021 ), the reaction mixture was stirred at 50° C. for 3 hours, and then cooled to room temperature. Acetic acid (17 ml) was added, and the solvent was evaporated in vacuo. The residue was diluted with ethyl acetate (1l), washed with saturated aqueous NaHCO$_3$ (500 ml). The organic portion was dried (MgSO$_4$), concentrated to afford the oily residue, which solidfied after storage at 5° C. overnight. The solid was washed with a mixture of diethyl ether and hexane (1:10) and dried to give (2S, 4R)-4-tert-butyldimethylsiloxy-2-hydroxymethyl-N-(4-nitrobenzyloxycarbonyl) pyrrolidine (38.2 g, 80% yield).

NMR(CDCl$_3$) δ: 0.04(3H,s),0.06(3H,s),0.86(9H,s),1.60~1.80(1H,m), 1.90~2.10(1H,m),3.50(2H,m),3.62(1H,m),3.76(1H,m),-4.20(1H,m)4.36(1H,m),5.28(2H,ABq,$J_{AB}$=14Hz,$\Delta$-$\nu_{AB}$=20Hz),7.50(2H,d,J=8Hz),8.24(2H,d,J=8Hz).

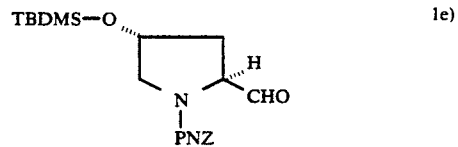
1e)

To a stirred mixture of molecular sieves dried DMSO (15.0 ml, 212 mmol) and dichloromethane (1.241 ) at −78° C. was added oxalyl chloride (10.0 ml, 114 mmol) dropwise over 5 minutes and stirring was continued for additional 10 minutes. To this solution was added a mixture of 1-(4-nitrobenzyloxycarbonyl) -2-hydroxymethyl-4-(tertbutyldimethylsiloxy) pyrrolidine (31.0 g, 75.6 mmol) and CH$_2$Cl$_2$ (155 ml) dropwise over 15 minutes and the stirring was continued for 30 minutes at the same temperature. After addition of Et$_3$N (52.5 ml, 377 mmol), removing of cold bath to warm to room temperature, washed with aqueous saturated NaHCO$_3$ (300 ml), dried (MgSO$_4$) of organic portion and concentrated in vacuo to afford the oily product which became solid after storage at room temperature. This crystalline product was washed with diethyl ether-hexane (1:10), collected by filtration and dried to give (2S, 4R)-4-tert-butyl-dimethylsiloxy-2-formyl-N-(4-nitrobenzyloxycarbonyl)pyrrolidine (29.7 g, 96% yield).

NMR(CDCl₃) δ:
0.08(3H,s),0.10(3H,s),0.86(9H,s),2.00(2H,m),3.60(2H,m),4.42(2H,m),5.24(2H,m),7.46and7.54(2H,each d,J=8Hz),8.24and8.26(2H,each d,J=8Hz),9.48and9.62(1H, each d,J=4Hz).

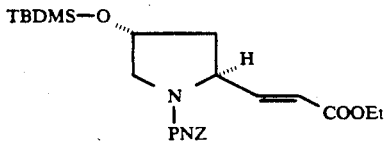
1f)

To a stirred mixture of the compound (29.7 g, 72.8 mmol) obtained in the above reaction and triethyl phosphonoacetate (19.1 ml, 96.3 mmol) in dioxane (300 ml) was added 60% NaH (3.49 g, 8.72 mmol) at 0° C. After being stirred for 1 hour at room temperature, the reaction mixture was diluted with ethyl acetate (300 ml) and washed successively with aqueous saturated NH₄Cl (100 ml) and brine (100 ml). The organic layer was dried (MgSO₄), concentrated and chromatographed on silica gel (Wakogel® C-300, ethyl acetate-hexane 1:3) to afford ethyl (E)-3-[(2S, 4R)-4-tert-butyldimethylsiloxy-N-(4-nitrobenzyloxycarbonyl) pyrrolidin-2-yl]acrylate (33.9 g, 97% yield).

NMR(CDCl₃) δ:
0.04(3H,s),0.06(3H,s),0.86(9H,s),1.26(3H,m),1.84(1H,m),2.08(1H,m),3.54(2H,m),4.18(2H,m),4.38(1H,m),4.60 (1H,m),5.22(2H,m),5.84and5.92(1H,each br d,J=16Hz),6.84and6.88(1H,each d,J=16Hz),7.48(2H,m),8.20(2H,m).

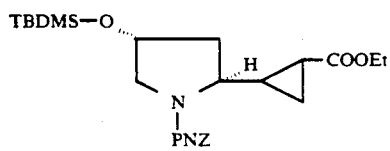
1g)

To a stirred solution of the compound (4.0 g, 8.4 mmol) obtained in the above reaction in diethyl ether (60 ml) at room temperature under N₂ atmosphere was added Pd(OAc)₂ (20 mg, 0.09 mmol) and the mixture stirred for 10 minutes. To this mixture was added a solution of diazomethane prepared from N-methyl-N-nitroso-p-toluenesulfonamide (21.5 g, 0.1 mol) in diethyl ether (300 ml) at 0° C.

After 1 hour with stirring, the ratio of starting material and the desired product was almost even. The reaction mixture was passed through the celite-pad to remove Pd(OAc)₂ and concentrated in vacuo. The oily residue was again treated with the same amount of diazomethane in the same manner to complete this reaction. After removal of Pd(OAc)₂, the reaction mixture was concentrated and subjected to column chromatography on silica gel (Wakogel® C-300, ethyl acetate-hexane 1:5) to afford ethyl trans-2-[(2S, 4R)-4-tert-butyldimethylsiloxy-N-( 4-nitrobenzyloxycarbonyl) pyrrolidin-2-yl]cyclopropanecarboxylate(2.17 g, 53% yield) as an oil.

NMR(CDCl₃) δ:
0.04(3H,s),0.06(3H,s),0.84(9H,s),1.22(3H,m),3.50(2H,m),4.12(2H,m),4.42(1H,m),5.22(2H,m),7.52(2H,m),8.22 (2H,d,J=8Hz)

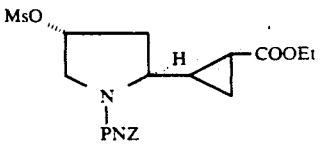
1h)

(i) A stirred solution of the compound (500 mg, 1.02 mmol) prepared in the above reaction in THF (5 ml) and CH₃CN (5 ml) was treated with 1N tetrabutyl ammonium fluoride in THF (1.0 ml, 1.0 mmol) at room temperature over 1 hour. The reaction mixture was poured into brine and taken up with ethyl acetate (30 ml×2). The organic layer was dried (MgSO₄) and concentrated to give ethyl trans-[(2S, 4R)-4-hydroxy-N-(4-nitrobenzyloxycarbonyl) pyrrolidin-2-yl]cyclopropanecarboxylate as a crude oil. (ii) A stirred solution of the crude oil product obtained above in CH₂Cl₂ (10 ml) was treated with methanesulfonyl chloride (0.23 ml, 2.97 mmol) and triethylamine (0.42 ml, 4.46 mmol) at 0° C. then at room temperature over 1 hour. The reaction mixture was poured into aqueous saturated NaHCO₃ (10 ml) and extracted with CH₂Cl₂ (30 ml×2). The organic layer was dried (MgSO₄), concentrated in vacuo and chromatographed on silica gel (Wakogel® C-300, ethyl acetate-hexane 1:1) to give ethyl trans-2-(2S, 4R)-4-methanesulfonyloxy-N-(4-nitrobenzyloxycarbonyl) pyrrolidin-2-yl]cyclopropanecarboxylate (485 mg, 100% yield) as an oil.

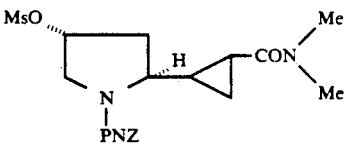
1i)

(i) To a stirred solution of the compound (480 mg, 1.05 mmol) obtained in the above reaction in MeOH (9.6 ml) was added 2N aqueous LiOH (1.0 ml, 2.0 mmol) and the stirring was continued for 12 hours.

After addition of 6N HCl (0.33 ml, 2.0 mmol), the reaction mixture was extracted with CH₂Cl₂(200 ml×2) and the organic layer dried (MgSO₄) and concentrated. (ii) A stirred solution of the residue obtained above in CH₂Cl₂ (9 ml) was treated with oxalyl chloride (0.27 ml, 3.1 mmol) and N,N-dimethylformamide (1 drop) at room temperature for 2 hours. The reaction mixture was evaporated and the residue was dissolved in benzene (3 ml), and evaporated again (repeated 3 times) to afford the crude acid chloride. (iii) To a stirred mixture of dimethylamine hydrochloride (260 mg, 3.2 mmol), THF (1.3 ml) and CH₂Cl₂ (9.0 ml) at room temperature was added triethylamine (0.47 ml, 3.2 mmol) and the stirring was continued for 5 minutes. After cooling to 0° C., a solution of the acid chloride obtained in the previous reaction in CH₂Cl₂ (3 ml) was added. The reaction mixture was stirred for 1 hour, poured into saturated aqueous NaHCO₃ (10 ml) and extracted with CH₂Cl₂ (20 ml×2). The organic layers were combined, dried (MgSO₄) and concentrated to afford trans-2-[(2S, 4R)-4-methanesulfonyloxy-N-(4-nitrobenzyloxycarbonyl) pyrrolidin-2-yl]-N,N-dimethylcyclopropanecarboxamide (356 mg, 74% yield).

NMR(CDCl₃) δ:
3.04(3H,s),5.26(2H,m),7.54(2H,m),8.24(2H,d,J=8Hz).

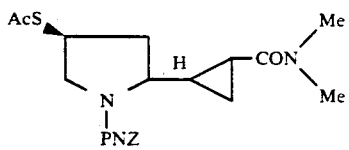

1j)

A mixture of the compound (350 mg, 0.77 mmol) obtained in the previous reaction, potassium thioacetate (263 mg, 2.30 mmol) and N,N-dimethylformamide (3.5 ml) was stirred at 70° C. for 1.5 hour. The reaction mixture was poured into H$_2$O (20 ml). Extraction with ethyl acetate (30 ml×2), drying (MgSO$_4$) and concentration in vacuo followed by column chromatography on silica gel (Wakogel ® C-300, ethyl acetate) to afford trans-2-[(2S, 4S)-4-acetylthio-N-(4-nitrobenzyloxycarbonyl)pyrrolidin2-yl]-N,N-dimethylcyclopropanecarboxyamide (225 mg, 67% yield).

REFERENCE 2 trans-2-(2S,4S)-4-Acetylthio-N-(4-nitrobenzyloxycarbonyl) pyrrolidin-2-yl]-N-methylcyclopropanecarboxamide

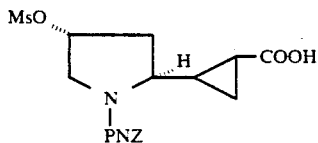

2a)

A stirred solution of ethyl trans-2-[(2S, 4R)-4-methanesulfonyloxy-N-(4-nitrobenzyloxycarbonyl)pyrrolidin-2-yl]cyclopropanecarboxylate (750 mg, 1.64 mmol) and MeOH (15 ml) was treated with 2N LiOH (2.4 ml, 4.8 mmol) at room temperature over 12 hours. The reaction mixture was neutralized with 6N HCl (0.80 ml, 4.8 mmol) and extracted with CH$_2$Cl$_2$ (20 ml×2). The organic layers were combined, dried (MgSO$_4$) and concentrated to afford trans-2-[(2S, 4R)-4-methanesulfonyloxy-N-(4-nitrobenzyloxycarbonyl)-pyrrolidin-2yl]cyclopropanecarboxylic acid (565 mg, 80% yield) as a residue.

NMR(CDCl$_3$) δ: 3.06(3H,s),5.28(2H,m),7.36(2H,m),8.20(2H,m).

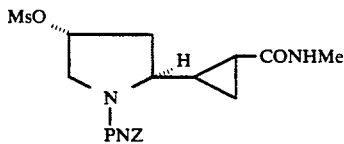

2b)

A stirred solution of trans-2-[(2S, 4R)-4-methanesulfonyloxy-N-(4-nitrobenzyloxycarbonyl)pyrrolidin-2-yl]cyclopropanecarboxylic acid (565 mg, 1.32 mmol) and CH$_2$Cl$_2$ (12 ml) was treated with oxalyl chloride (0.345 ml, 3.96 mmol) and N,N-dimethylformamide (1 drop) over 2 hours at room temperature.

The reaction mixture was dissolved in benzene (3 ml) and evaporated (repeated 3 times). A solution of the residue obtained in 2a) in CH$_2$Cl$_2$ (3 ml) was added to a solution of 40% aqueous methylamine (0.31 ml) in THF (12 ml) at 0° C. After continuous stirring for 1 hour, the reaction mixture was poured into saturated aqueous NaHCO$_3$ (30 ml), and extraced with ethyl acetate (30 ml×2). The organic layer was dried (MgSO$_4$) and concentrated in vacuo to afford trans-2-[(2S, 4R)-4-methanesulfonyloxy-N-(4-nitrobenzyloxycarbonyl)pyrrolidin-2-yl]-N-methylcyclopropanecarboxamide (340 mg, yield).

NMR(CDCl$_3$) δ: 3.04(3H,s),4.22(2H,m),7.32(2H,m),8.24(2H,m).

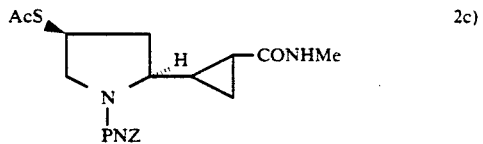

2c)

The same procedure as in REFERENCE 1j was carried out by using the compound (555 mg, 1.26 mmol) obtained in REFERENCE 2b to give the title compound (363 mg, 68% yield).

NMR(CDCl$_3$) δ: 2.36(3H,s),5.20(2H,br s),7.50(2H,br d,J=8Hz),8.24(2H, br d,J=8Hz).

REFERENCE 3 trans-2-(2S,4S)-4-Acetylthio-N-(4-nitrobenzyloxycarbonyl) pyrrolidin-2-yl]cyclopropanecarboxamide

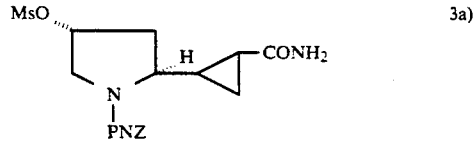

3a)

(i) A stirred solution of trans-2-[(2S, 4R)-4-methanesulfonyloxy-N-(4-nitrobenzyloxycarbonyl)pyrrolidin-2-yl]cyclopropanecarboxylic acid (1.0 g, 2.3 mmol) and CH$_2$Cl$_2$ (20 ml) was treated with oxalyl chloride (0.61 ml, 7.0 mmol) and N,N-dimethylformamide (1 drop) at room temperature over 2 hours. The reaction mixture was concentrated in reduced pressure and co-evaporated with benzene (3 times) to give the acid chloride. (ii) A solution of the acid chloride obtained in (i) and CH$_2$Cl$_2$ (2.0 ml) was added dropwise to a solution of 25% aqueous NH$_4$OH (0.65 ml, 2.3 mmol) in THF (10 ml) at 0° C. The reaction mixture was stirred at 0° C. for 15 minutes, poured into saturated aqueous NH$_4$Cl (20 ml) and extracted with CH$_2$Cl$_2$ (30 ml×2). The organic layers were combined, dried (MgSO$_4$) and concentrated to afford trans-2-[(2S, 4R)-4-methanesulfonyloxy-N-(4-nitrobenzyloxycarbonyl) pyrrolidin-2-yl]cyclopropanecarboxamide as a solid residue, which was used for the next step without further purification.

NMR(CDCl$_3$) δ: 3.04and3.05(3H,each s),5.24(2H,m),7.50(2H,m),8.24(2 H,d,J=8Hz).

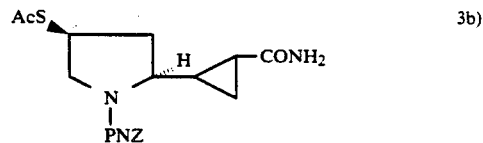

3b)

The same procedure as in REFERENCE 1j was carried out by using the compound (254 mg, 0.59 mmol) obtained in REFERENCE 3b to give the title compound (184 mg, 77% yield).

NMR(CDCl$_3$) δ: 2.34(3H,s),5.20(2H,br s),7.50(2H,br d,J=8Hz),8.26(2H, d,J=8Hz).

REFERENCE 4 trans-2-(2S,4S)-4-Acetylthio-N-(4-nitrobenzyloxycarbonyl) pyrrolidin-2-yl]cyclopropanecarboxamide diastereomer A and B

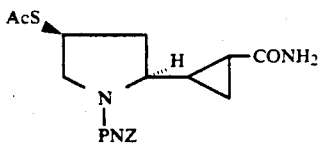

A mixture of trans-2-[(2S, 4R)-4-methanesulfonyloxy-N-(4-nitrobenzyloxycarbonyl)pyrrolidin-2-yl]cyclopropanecarboxamide (1.2 g, 2.8 mmol), potassium thioacetate (0.95 g, 8.3 mmol) and N,N-dimethylformamide (23 ml) was stirred at 70° C. for 3 hours. The reaction mixture was cooled to room temperature, poured into H$_2$O (20 ml) and extracted with ethyl acetate (40 ml). The organic layer was dried (MgSO$_4$), concentrated in reduced pressure and subjected to column chromatography on silica gel (Wakogel® C-300, CH$_2$Cl$_2$→1%MeOH in CH$_2$Cl$_2$→5% MeOH in CH$_2$Cl$_2$) to give the title compounds of the diastereomer B (less polar isomer, 452 mg, 39.5% yield), diastereomer A (polar isomer, 335 mg, 29.2% yield) and a mixture of two isomers (85 mg, 7.4% yield) as a powder. Diastereomer B NMR(CDCl$_3$) δ:
0.64(1H,m),1.36(2H,m),1.94(2H,m),2.36(3H,s),2.60(1H, m),3.38(2H,m),3.96(1H,m),4.12(1H,m),5.24(2H,br s), 7.56(2H,br d,J=8Hz),8.30(2H,d,J=8Hz).

Diastereomer A

NMR(CDCl$_3$) δ:
1.24(3H,m),1.84(2H,m),2.60(1H,m),2.34(3H,s),3.30(1H, m),3.64(1H,m),3.90(1H,m),4.12(1H,m),5.24(2H,m),7.54 (2H,br d,J=8Hz),8.24(2H,d,J=8Hz).

REFERENCE 5

(2S,4S)-4-Acetylthio-2-[trans-2-(4-nitrobenzyloxycarbonylaminomethyl) cyclopropyl]-N-(4-nitrobenzyloxycarbonyl)pyrrolidine

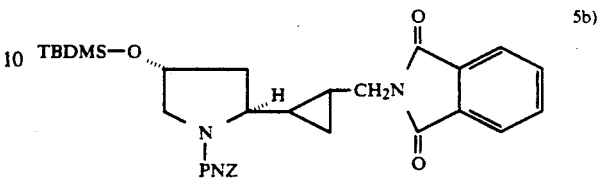

To a stirred mixture of ethyl trans-3-[(2S, 4R)-4-tert-butyldimethylsiloxy-N-(4-nitrobenzyloxycarbonyl)pyrrolidin-2-yl]cyclopropanecarboxylate (2.0 g, 4.1 mmol) and CH$_2$Cl$_2$ (100 ml) was added a solution of 25% diisobutylalminium hydride(DIBAL) in toluene (9.2 ml, 16.3 mmol) at −78° C. under N$_2$ atmosphere. Stirring was continued for 20 minutes and DIBAL (2.3 ml, 4.1 mmol) was added. After 30 minutes, acetic acid (1.3 ml, 21.5 mmol) was added and cooling bath was removed. The reaction mixture was diluted with ethyl acetate (300 ml) and washed with saturated aqueous sodium potassium tartrate (180 ml). The organic layer was dried (MgSO$_4$), concentrated and subjected to column chromatography on silica gel (Wakogel® C-300, 200 ml ethyl acetate-hexane 1:1) to afford (2S, 4R)-4-tert-butyldimethylsiloxy-2-[trans-2-(hydroxymethylcyclopropyl]-N-(4-nitrobenzyloxy-carbonyl) pyrrolidine (1.20 g, 66% yield).

NMR(CDCl$_3$) δ:
0.08(6H,s),0.44(2H,m),0.86(9H,s),0.80(2H,m),2.00(2H, m),3.20-3.80(4H,m),3.84(1H,m),4.42(1H,m),5.25(2H,m), 7.54(2H,m),8.24(2H,d,J=8Hz).

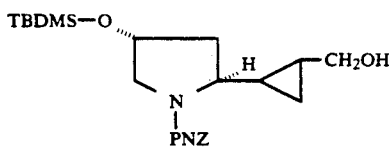

A solution of the compound (1.2 g, 2.7 mmol) obtained in the previous reaction in CH$_2$Cl$_2$ (24 ml) was treated with triethylamine (1.1 ml, 8.1 mmol) and mesyl chloride (0.41 ml, 5.4 mmol) over 30 minutes on an ice bath. The reaction mixture was poured into saturated aqueous NaHCO$_3$ and extracted with CH$_2$Cl$_2$ (twice). The combined organic layers were dried (MgSO$_4$) and concentrated in vacuo to give the mesylate.

A mixture of the mesylate and potassium phthalimide (0.74 g, 4.0 mmol) in dimethyl sulfoxide(DMSO) (12 ml) was stirred at 70° C. for 30 minutes. After cooling to room temperature, the reaction mixture was diluted with ethyl acetate (50 ml) and washed with H$_2$O (20 ml). The organic layer was dried (MgSO$_4$), concentrated and applied to column chromatography on silica gel (Wakogel® C-300, 200 ml, ethyl acetate-hexane 1:2) to afford (2S, 4R)-4-tert-butyldimethylsiloxy-2-[trans-2-(phthalimidomethyl)cyclopropyl]-N-(4-nitrobenzyloxycarbonyl)pyrrolidine (1.3 g, 82% yield).

NMR(CDCl$_3$) δ:
0.04(6H,s),0.40~1.10(4H,m),0.86(9H,s),1.90(2H,m), 3.20~3.60(4H,m),3.80(1H,m),4.40(1H,m),5.24(2H,m), 7.48-7.95(6H,m),8.20(2H,m).

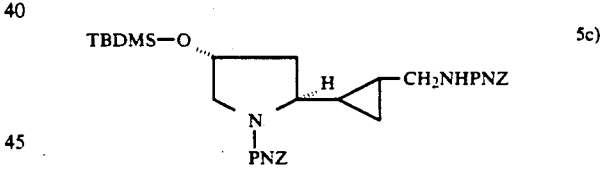

To a mixture of the compound (1.3 g, 2.2 mmol) obtained in the previous reaction in CH$_2$Cl$_2$ (13 ml) was added dropwise a mixture of 80% hydrazine hydrate (1.3 ml, 22 mmol) in MeOH (13 ml) at 0° C. The reaction mixture was then stirred at room temperature for 2 hours. After removal of the volatiles, the residue was taken up with ethyl acetate. The organic portion was washed with 10% NH$_4$OH, dried (MgSO$_4$) and concentrated to give the crude amine (736 mg, 75% yield).

A mixture of the crude amine in CH$_2$Cl$_2$ (14 ml) was treated with 4,6-dimethyl-2-(4-nitrobenzyloxycarbonylthio)pyrimidine (523 mg, 1.63 mmol) at room temperature over 1 hour. The reaction mixture was concentrated and applied to column chromatography on silica gel (Wakogel® C-300, 50 ml, ethyl acetate-hexane 1:2→1:1) to afford the diastereomer B (a less polar isomer, 280 mg, 20.4% yield) and the diastereomer A (a polar isomer, 502 mg, 36% yield) of (2S, 4R)-4-tert-butyldimethylsiloxy-2-[trans-2-(4-nitrobenzyloxycarbonylaminomethyl)cyclopropyl]-N-(4-nitrobenzyloxycarbonyl)pyrrolidine.

Diastereomer A (a polar isomer)

NMR(CDCl₃) δ:
0.08(6H,s),0.30~0.90(4H,m),0.86(9H,s),2.00(2H,m),
3.10~4.00(5H,m),4.40(1H,m),5.20(4H,m),7.50(4H,m),8-.22 (4H,m).

Diastereomer B (a less polar isomer) NMR(CDCl₃) δ:
0.08(6H,s),0.44(2H,m),0.50~0.90(2H,m),0.86(9H,s),
1.80~2
10(2H,m),3.20~3.70(4H,m),3.70~4.00(1H,m),4.40
(1H,m),5.20(4H,m),7.50(4H,m),8.20(4H,m).

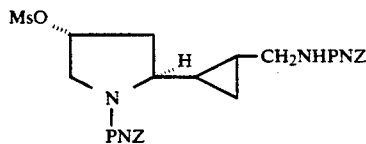

5d)

To a mixture of the diastereomer A (the polar isomer, 500 mg, 0.8 mmol) obtained in the previous reaction and MeOH (10 ml) was added 6N HCl (0.40 ml, 2.4 mmol) with stirring. After 1.5 hours, the reaction mixture was diluted with CH₂Cl₂ (30 ml) and washed with saturated aqueous NaHCO₃ (10 ml). The organic layer was dried (MgSO₄) and evaporated to give an oily residue.

A stirred mixture of the oily residue in CH₂Cl₂ (6.0 ml) was treated with triethylamine (0.31 ml, 2.2 mmol) and mesyl chloride (0.1 ml, 1.29 mmol) at 0° C. over 10 minutes. Usual aqueous work-up followed by column chromatography on silica gel (Wakogel ® C-300, ethyl acetate-hexane 2:1) to afford the diastereomer A of (2S, 4R)-4-methanesulfonyloxy-2-[trans-2-(4-nitrobenzyloxycarbonylaminomethyl) cyclopropyl]-N-(4-nitrobenzyloxycarbonyl)pyrrolidine (280 mg, 59% yield).

NMR(CDCl₃) δ:
0.50(2H,m),0.90(2H,m),2.00(1H,m),2.50(1H,m),3.06(3-H,
s),3.30~4.10(5H,m),5.24(5H,m),7.54(4H,m),8.24(4H,m-).

The same procedure as described above was carried out by using the diastereomer B (a less polar isomer, 280 mg, 0.44 mmol) obtained in REFERENCE 5c to give the diastereomer B of the 4-mesyloxypyrrolidine derivative (194 mg, 73% yield).

NMR(CDCl₃) δ:
0.50(2H,m),0.60~1.00(2H,m),2.10(1H,m),2.50(1H,m),
3.06
(3H,s),3.30~4.10(5H,m),5.24(5H,m),7.50(4H,m),8.20(4-H, m).

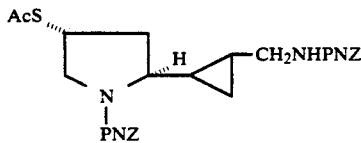

5e)

A mixture of the mesylate (the diastereomer A, 280 mg, 0.47 mmol) obtained in the previous reaction, potassium thiolacetate (162 mg, 1.42 mmol) and N,N-dimethylformamide(DMF) (5.6 ml) was stirred at 70° C. for 2 hours. Usual aqueous work-up (ethyl acetate-saturated aq NaCl) followed by column chromatography on silica gel (Wakogel ® C-300, ethyl acetate-hexane 1:1) gave the diastereomer A of (2S,4S)-4-acetylthio-2-[trans-2-(4-nitrobenzyloxycarbonylaminomethyl) cyclopropyl]-N-(4-nitrobenzyloxycarbonyl) pyrrolidine (232 mg, 86% yield).

NMR(CDCl₃) δ:
0.50(2H,m),0.70~1.10(2H,m),1.82(1H,m),2.50(2H,m),
2.90~4.20(5H,m),5.20(4H,m),7.50(4H,m),8.20(4H,m).

The same procedure as described above was carried out by using the mesylate (the diastereomer B, 190 mg, 0.32 mmol) obtained in REFERENCE 5d to give the diastereomer B of the 4-acetylthiopyrrolidine derivative (151 mg, 82% yield).

NMR(CDCl₃) δ:
0.50(2H,m),0.70~1.00(2H,m),1.80(1H,m),2.54(2H,m),
3.10~4.20(5H,m),5.20(4H,m),7.48(4H,m),8.18(4H,m).

What is claimed is:

1. A compound of the formula:

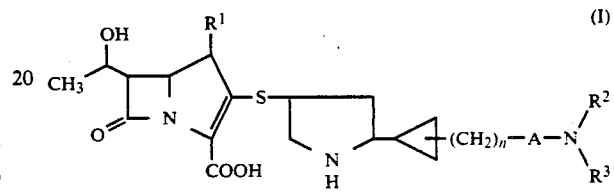

(I)

wherein $R_1$ is a hydrogen atom or a methyl group, each of $R^2$ and $R^3$ which may be the same or different, is a hydrogen atom or a lower alkyl group, or $R^2$ and $R^3$ form together with the adjacent nitrogen atom a heterocyclic group selected from the group consisting of an aziridinyl group, an azetidinyl group, a pyrrolidinyl group, a piperidino group, a piperazinyl group and a morpholino group, A is a carbonyl group or a single bond, and n is an integer of from 0 to 3; or a pharmaceutically acceptable salt or ester thereof.

2. The compound according to claim 1, wherein $R^1$ is a methyl group.

3. The compound according to claim 1, wherein each of $R^2$ and $R^3$ which may be the same or different is a hydrogen atom or a lower alkyl group.

4. The compound according to claim 1, wherein A is a carbonyl group.

5. The compound according to claim 1, which is: (1R,5S,6S)-2-[(2S,4S)-2-[2-(N,N-dimethylaminocarbonyl) cyclopropyl]pyrrolidin-4-ylthio]-6-[ (R)-1-hydroxyethyl]-1-methyl-1-carbapen-2-em-3-carboxylic acid, (1R,5S,6S)-6-[(R)-1-hydroxyethyl]-1-methyl-2-[(2S,4S)-2-[2-(N-methylaminocarbonyl)cyclopropyl]pyrrolidin-4-ylthio]-1-carbapen-2-em-3-carboxylic acid, (1R,5S,6S)-2-[(2S,4S)-2-[2-(aminocarbonyl) cyclopropyl]pyrrolidin-4-ylthio]-6-[(R)-1-hydroxyethyl]-1-methyl-1-carbapen-2-em-3-carboxylic acid, (5R,6S)-6-[(R)-1-hydroxyethyl]-2-[(2S,4S)-2-[2-(N-methylaminocarbonyl) cyclopropyl]pyrrolidin-4-ylthio]-1-carbapen-2 em-3-carboxylic acid, (1R,5S,6S)-2-[(2S,4S)-2-[2-(aminocarbonyl) cyclopropyl]pyrrolidin-4-ylthio]-6-[(R)-1-hydroxyethyl]-1-methyl-1-carbapen-2-em-3-carboxylic acid, (1R,5S,6S)-2-[(2S,4S)-2-[2-(aminomethyl) cyclopropyl]pyrrolidin-4-ylthio]-6-[(R)-1-hydroxyethyl]-1-methyl-1-carbapen-2-em-3-carboxylic acid, (5R,6S)-2-[(2S,4S)-2-[2-(aminomethyl) cyclopropyl]pyrrolidin-4-ylthio]-6-[(R)-1-hydroxyethyl]-1-carbapen-2-em-3-carboxylic acid, or (1R,5S,6S)-2-[(2S,4S)-2-(2-aminocyclopropyl)pyrrolidin-4-ylthio]-6-[(R)-1-hydroxyethyl]-1-methyl-1-carbapen-2-em3-carboxylic acid.

6. A compound of the formula:

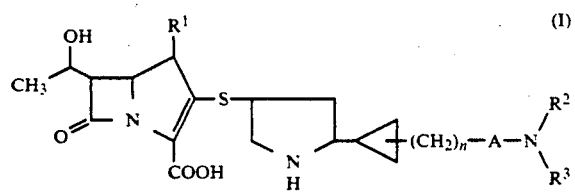

wherein R[1] is a hydrogen atom or a methyl group, each of R[2] and R[3] which may be the same or different, is a hydrogen atom or a lower alkyl group, or R[2] and R[3] form together with the adjacent nitrogen atom a heterocyclic group selected from the group consisting of an aziridinyl group, an azetidinyl group, a pyrrolidinyl group, a piperidino group, a piperazinyl group and a morpholino group, A is a carbonyl group or a single bond, and n is an integer of from 0 to 3, with the proviso that when R[2] and R[3] form together with the adjacent nitrogen atom the azetidinyl group, A is not a carbonyl group; or a pharmaceutically acceptable salt or ester thereof.

7. An antibacterial agent comprising an antibacterially effective amount of the compound of the formula:

wherein R[1] is a hydrogen atom or a methyl group, each of R[2] and R[3] which may be the same or different is a hydrogen atom or a lower alkyl group, or R[2] and R[3] form together with the adjacent nitrogen atom, a heterocyclic group selected from the group consisting of an aziridinyl group, an azetidinyl group, a pyrrolidinyl group, a piperidino group, a piperazinyl group and a morpholino group, A is a carbonyl group or a single bond, and n is an integer of from 0 to 3; or a pharmaceutically acceptable salt or ester thereof, and a pharmaceutically acceptable carrier or diluent.

8. A method for the treatment of infectious diseases caused by pathogenic bacteria which comprises administering an antimicrobially effective amount of the compound of claim 1 to a human being or animal.

* * * * *

UNITED STATES PATENT AND TRADEMARK OFFICE
CERTIFICATE OF CORRECTION

PATENT NO. : 5,112,818

DATED : May 12, 1992

INVENTOR(S) : Susumu Nakagawa et al.

It is certified that error appears in the above-identified patent and that said Letters Patent is hereby corrected as shown below:

Title page, and col. 1, lines 1-2, should read

--2-(2-CYCLOPROPYLPYRROLIDIN-4-YLTHIO)CARBAPENEM DERIVATIVES--.

Signed and Sealed this

Third Day of August, 1993

Attest:

MICHAEL K. KIRK

*Attesting Officer*      Acting Commissioner of Patents and Trademarks